US011753635B2

(12) United States Patent
Ismagilov et al.

(10) Patent No.: US 11,753,635 B2
(45) Date of Patent: *Sep. 12, 2023

(54) METHODS AND SYSTEMS AND RELATED COMPOSITIONS FOR MIXTURES SEPARATION WITH A SOLID MATRIX

(71) Applicant: CALIFORNIA INSTITUTE OF TECHNOLOGY, Pasadena, CA (US)

(72) Inventors: Rustem Ismagilov, Altadena, CA (US); Erik Jue, Pasadena, CA (US); Daan Witters, San Diego, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/511,235

(22) Filed: Oct. 26, 2021

(65) Prior Publication Data
US 2022/0049242 A1    Feb. 17, 2022

Related U.S. Application Data

(62) Division of application No. 16/132,235, filed on Sep. 14, 2018, now Pat. No. 11,174,477.
(Continued)

(51) Int. Cl.
*C12N 15/10* (2006.01)
*B01L 3/00* (2006.01)
(Continued)

(52) U.S. Cl.
CPC .......... *C12N 15/1003* (2013.01); *B01L 3/508* (2013.01); *B01L 3/50851* (2013.01); *B01L 3/502753* (2013.01); *B01L 7/52* (2013.01); *C12N 15/1006* (2013.01); *C12N 15/1013* (2013.01); *C12Q 1/6806* (2013.01); *G01N 21/6428* (2013.01); *G01N 21/6456* (2013.01); *B01L 2200/0631* (2013.01); *B01L 2200/0689* (2013.01); *B01L 2300/04* (2013.01); *B01L 2300/069* (2013.01);
(Continued)

(58) Field of Classification Search
CPC ............ C12N 15/1006; C12N 15/1003; C12N 15/1013; C12Q 1/6806; B01L 3/502753; B01L 2200/0631; B01L 2300/069
See application file for complete search history.

(56) References Cited

U.S. PATENT DOCUMENTS 11,149,265 B2   10/2021   Ismagilov et al.
11,174,477 B2   11/2021   Ismagilov et al.
(Continued)

OTHER PUBLICATIONS 5 reasons why pandemics like COVID-19 are becoming more likely, Gavi:The Vaccine Alliance. Apr. 28, 2020. Downloaded on Nov. 5, 2021. Available online from www.gavi.org/vaccineswork/5-reasons-why-pandemics-like-covid-19-are-becoming-more-likely. 5 Pages.
(Continued)

*Primary Examiner* — Jezia Riley
(74) *Attorney, Agent, or Firm* — Steinfl + Bruno LLP

(57) ABSTRACT

Methods and systems and related compositions for separating through a solid matrix a mixture comprising a nucleic acid together with a target compound having a water solubility equal to or greater than 0.01 mg per 100 mL, which can be used for managing fluid flow, biochemical reactions and purification of the nucleic acid or other target analytes.

41 Claims, 8 Drawing Sheets

Related U.S. Application Data

(60) Provisional application No. 62/558,679, filed on Sep. 14, 2017.

(51) Int. Cl.
  *C12Q 1/6806* (2018.01)
  *B01L 7/00* (2006.01)
  *G01N 21/64* (2006.01)

(52) U.S. Cl.
  CPC ... *B01L 2300/0672* (2013.01); *B01L 2300/18* (2013.01); *B01L 2400/0605* (2013.01)

(56) References Cited

U.S. PATENT DOCUMENTS

| | | |
|---|---|---|
| 2008/0090287 A1 | 4/2008 | Larsen |
| 2015/0182966 A1 | 7/2015 | Coursey et al. |
| 2017/0095814 A1 | 4/2017 | Boehm et al. |
| 2019/0078080 A1 | 3/2019 | Ismagilov |
| 2022/0098573 A1 | 3/2022 | Ismagilov et al. |

OTHER PUBLICATIONS

Cephid, Molecular Diagnostics. Home page + Mission Page. Downloaded on Nov. 5, 2021. Available online from www.cepheid.com/en_US/personas/laboratory-professionals. 22 Pages.

Gill, V., "Coronavirus:This is not the last pandemic," BBC News, Jun. 6, 2020. Downloaded on Nov. 5, 2021. Available online from www.bbc.com/news/science-environment-52775386.10 Pages.

Hilsenrath, J., "Global Viral Outbreaks Like Coronavirus, Once Rare, Will Become More Common; Urbanization, globalization and increased human consumption of animal proteins are driving a rise in epidemics" Wall street Journal. Mar. 6, 2020. 6 pages. Available online from www.wsj.com/articles/viral-outbreaks-once-rare-become-part-of-the-global-landscape-11583455309.

World Health Organization Coronavirus Dashboard, Global Information as of Nov. 4, 2021. Downloaded on Nov. 5, 2021. Available online from internet: covid19.who.int/. 1 Page.

Restriction Requirement for U.S. Appl. No. 17/131,449, filed Dec. 22, 2020, on behalf of California Institute of Technology. dated Jul. 8, 2022. 8 Pages.

Definition of "kit" by Merriam Webster dictionary. Downloaded from web.archive.org with a date of Aug. 17, 2017. 12 pages.

Heo et al., A valveless rotary microfluidic device for multiplex point mutation identification based on ligation-rolling circle amplification, Nov. 14, 2015, Biosensors and Bioelectronics, 78, pp. 140-146.

Lai, et al., Calibration Curves for Real-Time PCR. Molecular Diagnostics and Genetics, Clinical Chemistry, 51:7, 1132-1136 (2005).

Non-Final Office Action for U.S. Appl. No. 17/131,449, filed Dec. 22, 2020, on behalf of California Institute of Technology. dated Dec. 29, 2022. 16 Pages.

Non-Final Office Action issued for U.S. Appl. No. 17/473,832, filed Sep. 13, 2021 on behalf California Institute of Technology. dated Mar. 22, 2023. 13 pages.

Sedlak, R.H. et al., A multiplexed droplet digital PCR assay performs better than qPCR on inhibition prone samples. Diagnostic Microbiology and Infectious Disease, vol. 80, Issue 4, Dec. 2014, pp. 285-286. 3 pages.

Tang, Yi-Wei, et al. Molecular diagnostics of infectious diseases. Clinical Chemistry, 43:11, pp. 2021-2038. (1997).

Wiktionary, definition of "rxn". Downloaded through the Wayback Machine, dated Oct. 2, 2015. 1 page.

Zymo Research, Quick-DNA/RNA Viral 96 Kit. Downloaded Mar. 15, 2023. 3 pages. Website: www.zymoresearch.com/products/quick-dna-rna-viral-96-kit.

Notice for Allowance for U.S. Appl. No. 17/131,449, filed Dec. 22, 2020, on behalf of California Institute of Technology, dated May 10, 2023. 8 Pages.

Notice of Allowance issued for U.S. Appl. No. 17/473,832, filed Sep. 13, 2021 on behalf California Institute of Technology, dated Jun. 26, 2023. 10 pages.

METHODS AND SYSTEMS AND RELATED COMPOSITIONS FOR MIXTURES SEPARATION WITH A SOLID MATRIX

CROSS REFERENCE TO RELATED APPLICATION

The present application is a divisional of U.S. application Ser. No. 16/132,235, entitled "Methods and Systems and Related Compositions for Mixtures Separation with a Solid Matrix", filed on Sep. 14, 2018, which in turn, claims priority of U.S. Provisional Application No 62/558,679, entitled "Methods and Device for Purification and Detection of Analytes," filed on Sep. 14, 2017, the entire disclosure of each of which is incorporated herein by reference. This application may be related to PCT International Application PCT/US18/51201 filed on Sep. 14, 2018 and entitled "Methods And Systems And Related Compositions For Mixtures Separation With A Solid Matrix," and to U.S. application Ser. No. 16/130,810 filed on Sep. 13, 2018 and entitled "Purification and Detection of Analytes" and PCT International Application PCT/US18/50919 filed on Sep. 13, 2018 and entitled "Purification and Detection of Analytes" the entire disclosures of each of which are herein incorporated by reference in its entirety.

STATEMENT OF GOVERNMENT GRANT

This invention was made with government support under Grant No. HR0011-11-2-0006 awarded by DARPA and under Grant No. W15QKN-16-9-1002 awarded by the Defense Threat Reduction Agency. The government has certain rights in the invention.

FIELD

The present disclosure generally relates to biochemistry and molecular biology, and more specifically to methods and systems and related compositions for separation of mixtures with a solid matrix.

BACKGROUND

In the biochemistry and molecular biology fields, several processes and reactions involve separation of mixtures of one or more analytes alone or in combination with additional compounds, wherein the separation is performed with a solid matrix.

In particular, in the above fields several processes and reactions involve separation of mixtures where nucleic acid is comprised typically as an analyte, together with additional compounds.

However, despite the advancement of the technology, performing an efficient and effective matrix separation of mixtures comprising nucleic acids through a solid matrix, remains challenging in particular when the separation is directed to provide the nucleic acid as a substrate for further biochemical reactions.

SUMMARY

Provided herein, are methods and systems and related compositions that can be used to separate a solution comprising a nucleic acid together with an additional compound, which in several embodiments allow purification of nucleic acid while minimizing rehydration of the separated nucleic acid.

According to a first aspect, a method and a system are described to selectively remove from a solid matrix, a target compound absorbed to the solid matrix and having a water solubility equal to or greater than 0.001 g per 100 mL the solid matrix further retaining a nucleic acid.

The method comprises: contacting the solid matrix with a target compound removing agent having a water solubility equal to or less than 10 g per 100 mL with water having a solubility in the removing agent of less than 30 g per 100 mL. In the method the contacting is performed for a time and under condition to remove the target compound from the solid matrix.

The system comprises a target compound removing agent having a water solubility equal to or less than 10 g per 100 mL with water having a solubility in the removing agent of less than 30 g per 100 mL; and a solid matrix configured to absorb a nucleic acid.

According to a second aspect, a method and a system are described to selectively capture a nucleic acid in a solid matrix.

The method comprises: contacting the solid matrix with a solution comprising the nucleic acid together with a target compound having a water solubility equal to or greater than 0.001 g per 100 mL; and contacting the solid matrix with a target compound removing agent having a water solubility equal to or less than 10 g per 100 mL with water having a solubility in the removing agent of less than 30 g per 100 mL.

In the method, contacting the solid matrix with a solution comprising the nucleic acid is performed for a time and under condition to allow absorbance of the nucleic acids to the solid matrix. In the contacting, the solid matrix with a target compound removing agent is performed for a time and under condition to remove the target compound from the solid matrix thus capturing the nucleic acid in the solid matrix.

The system comprises a target compound removing agent having a water solubility equal to or less than 10 g per 100 mL with water having a solubility in the removing agent of less than 30 g per 100 mL; and a solid matrix configured to absorb a nucleic acid.

According to a third aspect, a method and a system are described to separate a nucleic acid from a mixture further comprising an additional target compound.

The method comprises capturing the nucleic acid in a solid matrix by performing any one of the methods to capture a nucleic acid herein described; and eluting the captured nucleic acid from the solid matrix.

The system comprises a target compound removing agent having a water solubility equal to or less than 10 g per 100 mL with water having a solubility in the removing agent of less than 30 g per 100 mL; and a nucleic acid removing agent.

According to a fourth aspect, a method and a system are described to perform a biochemical reaction of a nucleic acid.

The method comprises capturing the nucleic acid in a solid matrix by performing any one of the methods to capture a nucleic acid herein described; eluting the captured nucleic acid from the solid matrix; and contacting the eluted nucleic acid with a suitable reagent to perform the biochemical reaction.

The system comprises a target compound removing agent having a water solubility equal to or less than 10 g per 100 mL with water having a solubility in the removing agent of less than 30 g per 100 mL; and at least one of a solid matrix configured to absorb a nucleic acid and a reagent to perform the biochemical reaction.

Methods and systems herein described and related compositions, in several embodiments can be used to perform an effective and selective solid matrix separation of a nucleic acid from a sample further including target compounds such as impurities retained in the solid matrix.

Methods and systems herein described and related compositions, in several embodiments can be used to perform nucleic acid purification which reduces and in particular minimizes presence in the separated nucleic acid of compounds capable of inhibiting a biochemical reaction of the separated nucleic acid.

Accordingly, methods and systems herein described and related compositions, in several embodiments can be used to perform amplification and/or any other biochemical reactions of a nucleic acid from a sample or other mixture where the nucleic acid is comprised together with additional compounds.

The methods and systems herein described and related compositions can be used in connection with various applications wherein separation of mixtures comprising a nucleic acid together with other compounds is desired. For example, methods and systems herein described and related composition can be used in application to detect and/or amplify nucleic acid from mixtures such as processed or unprocessed samples. Additional exemplary applications include separation and/or uses of the separated nucleic acid and/or target compounds in several fields including basic biology research, applied biology, bio-engineering, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein.

DETAILED DESCRIPTION

Figure 1:
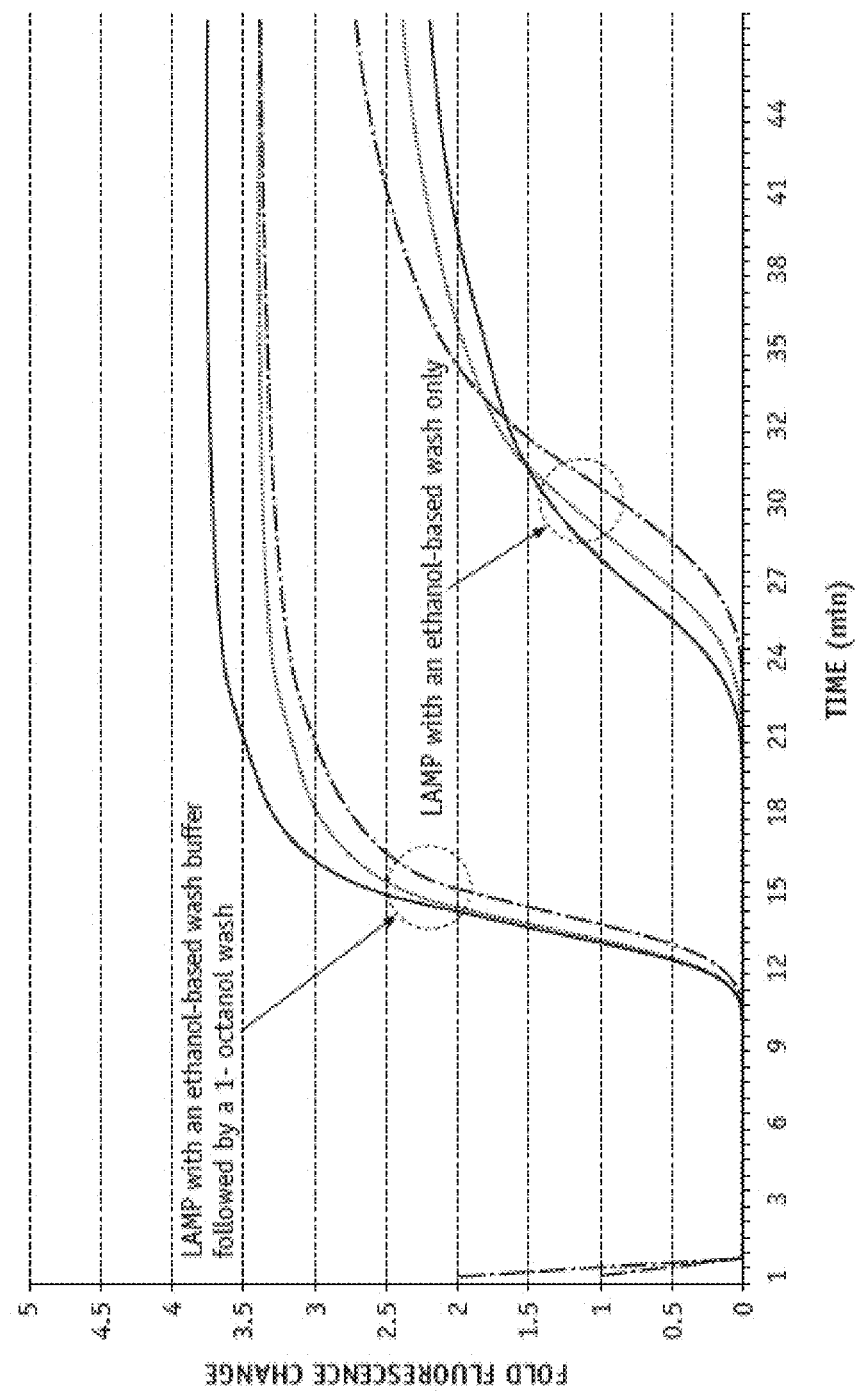
FIG. 1 shows a chart illustrating nucleic acid amplification curves for loop-mediated isothermal amplification (LAMP) performed on a nucleic acid separated from an initial mixture after an ethanol-based wash only or ethanol-based wash buffer followed by a 1-octanol wash each in triplicate (n=3).

Provided herein are methods and systems and related compositions that can be used to separate a mixture comprising a nucleic acid together with a target compound.

The term "separate" or "separation" as used herein indicate a process converting a source mixture of chemical substances into two or more distinct product mixtures. In particular, in embodiments herein described, the source mixture is a solution comprising the nucleic acid. In separations in the sense of the disclosure the conversion of the mixture into distinct product mixtures is performed based on difference in physical and/or chemical properties of the components of the mixture, such as shape, mass, density, size, chemical affinity and/or additional physical and/or chemical properties of the components of the solution identifiable by a skilled person.

In a separation according to the disclosure at least one of the product mixtures is typically enriched in one or more components of the starting mixture, typically the nucleic acid. In some cases, in at least one product mixture provided in outcome of a separation in accordance with the disclosure, the presence of the one or more component of the source mixture is maximized while the presence of other components of the starting mixture is minimized. In those cases, the separation can result in a complete division of the one or more components of the source mixture, typically the nucleic acid, from the other components and therefore in the related purification.

Exemplary mixtures in the sense of the disclosure comprise processed or unprocessed samples of an environment provided for use in testing, examination, or study. The environment can comprise a biological environment including living beings and in particular human beings.

The term "sample" as used herein indicates a limited quantity of something that is indicative of a larger quantity of that something, including but not limited to fluids from the biological environment, such as tissues, organs or other biological material from the living being such as urethra, urine, cervix, vagina, rectum, oropharynges, conjunctiva, or any body fluids, cultures, tissues, commercial recombinant proteins, synthetic compounds or portions thereof. Exemplary biological samples comprise: cheek tissue, whole blood, dried blood spots, organ tissue, plasma, urine, mucus, mucosal secretions, vaginal fluids and secretions, urethral fluids and secretions, feces, skin, hair, or tumor cells, among others identifiable by a skilled person. Biological samples can be obtained using sterile techniques or non-sterile techniques, as appropriate for the sample type, as identifiable by persons skilled in the art. Some biological samples can be obtained by contacting a swab with a surface on a human body and removing some material from said surface, examples include throat swab, urethral swab, oropharyngeal swab, cervical swab, vaginal swab, genital swab, anal swab.

Typically, a biological sample provided for use in testing, examination, or study. is further processed with agents which are selected to allow and/or facilitate the intended testing examination or study. Exemplary agents comprise a buffer agent which is a chemical compound that is capable of maintain the pH value stability of an aqueous solution, or a chaotropic agent which a molecule in water solution that can disrupt the hydrogen bonding network between water molecules and can be used to disrupt membrane integrity of a cell. Additional agents used to treat a biological sample comprise a biological medium, an antibiotic, and additional agents identifiable by a skilled person in view of the intended use of the biological sample. Depending on the type of biological sample and the intended analysis, biological samples can be used freshly for sample preparation and analysis, stored at room temperature, stored under refrigeration, stored frozen, treated with a lysis solution and then stored, or fixed using fixative. For example, urine can be mixed with specimen transport and storage tube (see e.g. Aptima® Urine Specimen Transport Tube and additional commercially available containers).

In methods and systems herein described a separation of a mixture of nucleic acid and target compound in the sense of the disclosure can be performed for analytical purposes, and therefore be directed to qualitatively or quantitatively detect at least one component of the source mixture, typically the nucleic acid. A separation in the sense of the disclosure can be performed for preparative purposes, and therefore be directed to prepare fractions of the mixture components, typically the nucleic acid, that can be saved and/or used to perform additional reactions.

In particular, in several embodiments of the disclosure the separation can be performed to detect and/or purify the nucleic acid component of the source mixture while removing the target compound from the mixture.

The term "nucleic acid" "NA" or "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. Accordingly, the term "polynucleotide" includes nucleic acids of any length, and in particular DNA, RNA, and fragments thereof. A "nucleotidic oligomer" or "oligonucleotide" as used herein refers to a polynucleotide of three or more but equal to or less than 300 nucleotides.

The term "DNA" or "deoxyribonucleic acid" as used herein indicates a polynucleotide composed of deoxyribonucleotide bases or an analog thereof to form an organic polymer. The term "deoxyribonucleotide" refers to any compounds that consist of a deoxyribose (deoxyribonucleotide) sugar joined to a purine or pyrimidine base and to a phosphate group, and that are the basic structural units of a deoxyribonucleic acid, typically adenine (A), cytosine (C), guanine (G), and thymine (T). In an DNA adjacent ribose nucleotide bases are chemically attached to one another in a chain typically via phosphodiester bonds. The term "deoxyribonucleotide analog" refers to a deoxyribonucleotide in which one or more individual atoms have been replaced with a different atom with a different functional group. For example, deoxyribonucleotide analogues include chemically modified deoxyribonucleotides, such as methylation hydroxymethylation glycosylation and additional modifications identifiable by a skilled person.

The term "RNA" or "ribonucleic acid" as used herein indicates a polynucleotide composed of ribonucleotide bases or an analog thereof linked to form an organic polymer. The term "ribonucleotide" refers to any compounds that consist of a ribose (ribonucleotide) sugar joined to a purine or pyrimidine base and to a phosphate group, and that are the basic structural units of a ribonucleic acid, typically adenine (A), cytosine (C), guanine (G), and uracil (U). In an RNA adjacent ribose nucleotide bases are chemically attached to one another in a chain typically via phosphodiester bonds.

The term "target compound" as used herein indicates a substance other than a nucleic acid formed by two or more chemical elements chemically bonded together. Typically, chemical bonds holding elements in a target compound in the sense of the disclosure comprise covalent bonds and non covalent bonds. The term "bond", "bind", "binding", as used herein indicates an attractive interaction between two elements which results in a stable association of the element in which the elements are in close proximity to each other. If each element is comprised in a molecule the result of binding is typically formation of a molecular complex. Attractive interactions in the sense of the present disclosure refer to non-covalent binding. Non-covalent bonding includes ionic bonds, hydrophobic interactions, electrostatic interactions, hydrogen bonds, and dipole-dipole bonds. Electrostatic interactions include association between two oppositely charged entities.

A target compound in the sense of the disclosure can comprise any inorganic or organic compound, wherein the term inorganic compound indicates a chemical compound that lacks C—H bonds, while the term "organic compound" indicates any chemical compound that contains carbon.

Accordingly, target inorganic compounds in the sense of the disclosure typically comprise inorganic salts composed of a metal ion (cation) and a non-metal ion (anion). Exemplary inorganic salts comprise binary salts such as calcium fluoride ($CaF2$), ternary salts wherein a metal ion combines with a polyatomic anion PAA, such as NaCl, $MgCl2$, KCl, KNO2, KNO3, $MgSO4$, or other inorganic salts identifiable by a skilled person.

A target organic compound in the sense of the disclosure typically comprises aliphatic or aromatic compounds and/or organic molecules comprising aliphatic and/or aromatic groups.

As used herein, the term "aliphatic" refers to an alkyl, alkenyl or alkynyl compound or group which can be a substituted unsubstituted and/or heteroatom containing, linear, branched or cyclic and can further be heteroatom containing. As used herein the term "alkyl" as used herein refers to a linear, branched, or cyclic, saturated hydrocarbon group formed by a carbon chain. As used herein the term "carbon chain" indicates a linear or branched line of connected carbon atoms. An alkyl carbon chain typically although not necessarily containing 1 to about 18 carbon atoms. As used herein the term "alkenyl" indicates a linear, branched, or cyclic hydrocarbon group that contains at least one carbon-carbon double bond. As used herein the term "alkynyl" indicates a linear, branched, or cyclic hydrocarbon group that contains at least one carbon-carbon triple bond.

As used herein the term "aromatic" refers to a chemical compound or group containing a conjugated planar ring system with delocalized pi electron clouds instead of discrete alternating single and double bonds, such as an aryl or aralkyl compound which can be substituted or unsubstituted and/or heteroatom containing as will be understood by a skilled person. The term "aryl" as used herein, and unless otherwise specified, refers to an aromatic compound containing a single aromatic ring or multiple aromatic rings that are fused together, directly linked, or indirectly linked (such that the different aromatic rings are bound to a common group such as a methylene or ethylene moiety). Preferred aryl groups contain 5 to 12 carbon atoms, and particularly preferred aryl groups contain 5 to 6 carbon atoms. Exemplary aryl groups contain one aromatic ring or two fused or linked aromatic rings, e.g., phenyl, naphthyl, biphenyl, diphenylether, diphenylamine, benzophenone, and the like.

Unless otherwise indicated, the term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents. As used herein, a "substituent" is an atom or group of atoms substituted in place of a hydrogen atom on the main chain of a hydrocarbon, which can form a functional group.

The term "functional group" as used herein indicates specific groups of atoms within a molecular structure that are responsible for a characteristic chemical and physical property of that structure. Exemplary functional groups comprise hydroxyl, sulfhydryl, $C_1$-$C_{12}$ alkoxy, $C_2$-$C_{12}$ alkenyloxy, $C_2$-$C_{12}$ alkynyloxy, $C_5$-$C_{12}$ aryloxy, $C_6$-$C_{12}$ aralkyloxy, $C_6$-$C_{12}$ alkaryloxy, acyl (including $C_2$-$C_{12}$ alkylcarbonyl (—CO-alkyl) and $C_6$-$C_{12}$ arylcarbonyl (—CO-aryl)), acyloxy (—O-acyl, including $C_2$-$C_{12}$ alkylcarbonyloxy (—O—CO-alkyl) and $C_6$-$C_{12}$ arylcarbonyloxy (—O—CO-aryl)), $C_2$-$C_{12}$ alkoxycarbonyl (—(CO)—O-alkyl), $C_6$-$C_{12}$ aryloxycarbonyl (—(CO)—O-aryl), $C_2$-$C_{12}$ alkylcarbonato (—O—(CO)—O-alkyl), $C_6$-$C_{12}$ arylcarbonato (—O—(CO)—O-aryl), carboxy (—COOH), carboxylato (—COO$^-$), carbamoyl (—(CO)—$NH_2$), mono-($C_1$-$C_{12}$ alkyl)-substituted carbamoyl (—(CO)—NH($C_1$-$C_{12}$ alkyl)), di-($C_1$-$C_{12}$ alkyl)-substituted carbamoyl (—(CO)—N($C_1$-$C_{12}$ alkyl)$_2$), mono-($C_5$-$C_{12}$ aryl)-substituted carbamoyl (—(CO)—NH-aryl), di-($C_5$-$C_{12}$ aryl)-substituted carbamoyl (—(CO)—N($C_5$-$C_{12}$ aryl)$_2$), di-N—($C_1$-$C_6$ alkyl), N—($C_5$-$C_{12}$ aryl)-substituted carbamoyl, thiocarbamoyl (—(CS)—$NH_2$), mono-($C_1$-$C_{12}$ alkyl)-substituted thiocarbamoyl (—(CO)—NH($C_1$-$C_{12}$ alkyl)), di-($C_1$-$C_{12}$ alkyl)-substituted thiocarbamoyl (—(CO)—N($C_1$-$C_6$ alkyl)$_2$), mono-($C_5$-$C_{12}$ aryl)-substituted thiocarbamoyl (—(CO)—NH-aryl), di-($C_5$-$C_6$ aryl)-substituted thiocarbamoyl (—(CO)—N($C_5$-$C_6$ aryl)$_2$), di-N—($C_1$-$C_6$ alkyl), N—($C_5$-$C_6$ aryl)-substituted thiocarbamoyl, carbamido (—NH—(CO)—$NH_2$), cyano cyanato thiocyanato formyl (—(CO)—H), thioformyl (—(CS)—H), amino (—$NH_2$), mono-($C_1$-$C_{12}$ alkyl)-substituted amino, di-($C_1$-$C_{12}$ alkyl)-substituted amino, mono-($C_5$-$C_{12}$ aryl)-substituted amino, di-($C_5$-$C_6$ aryl)-substituted amino, $C_2$-$C_{12}$ alkylamido (—NH—($C_0$)-alkyl), $C_6$-$C_{12}$ arylamido (—NH—(CO)-aryl), imino (—CR=NH where R=hydrogen, $C_1$-$C_{12}$ alkyl, $C_5$-$C_{12}$ aryl, $C_6$-$C_{12}$ alkaryl, $C_6$-$C_{12}$ aralkyl, etc.), $C_2$-$C_{12}$ alkylimino (—CR=N(alkyl), where R=hydrogen, $C_1$-$C_{12}$ alkyl, $C_5$-$C_{12}$ aryl, $C_6$-$C_{12}$ alkaryl, $C_6$-$C_2$ aralkyl, etc.), arylimino (—CR=N(aryl), where R=hydrogen, $C_1$-$C_{12}$ alkyl, $C_5$-$C_{12}$ aryl, $C_6$-$C_{12}$ alkaryl, $C_6$-$C_{12}$ aralkyl, etc.), nitro (—$NO_2$), nitroso (—NO), sulfo (—$SO_2$—OH), sulfonato (—$SO_2$—O$^-$, $C_1$-$C_{12}$ alkylsulfanyl (—S-alkyl; also termed "alkylthio"), $C_5$-$C_{12}$ arylsulfanyl (—S-aryl; also termed "arylthio"), $C_1$-$C_{12}$ alkylsulfinyl (—(SO)-alkyl), $C_5$-$C_{12}$ arylsulfinyl (—(SO)-aryl), $C_1$-$C_{12}$ alkylsulfonyl (—$SO_2$-alkyl), $C_5$-$C_{12}$ arylsulfonyl (—$SO_2$-aryl), boryl (—$BH_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—$PO_2$), phosphino (—$PH_2$), silyl (—$SiR_3$ wherein R is hydrogen or hydrocarbyl), and silyloxy (—O-silyl); and the hydrocarbyl moieties $C_1$-$C_{12}$ alkyl (preferably $C_1$-$C_{12}$ alkyl, more preferably $C_1$-$C_6$ alkyl), $C_2$-$C_{12}$ alkenyl (preferably $C_2$-$C_{12}$ alkenyl, more preferably $C_2$-$C_6$ alkenyl), $C_2$-$C_{12}$ alkynyl (preferably $C_2$-$C_{12}$ alkynyl, more preferably $C_2$-$C_6$ alkynyl), $C_5$-$C_{12}$ aryl (preferably $C_5$-$C_{12}$ aryl), $C_6$-$C_{12}$ alkaryl (preferably $C_6$-$C_{12}$ alkaryl), and $C_6$-$C_{12}$ aralkyl (preferably $C_6$-$C_{12}$ aralkyl), halo (such as F, $C_1$, Br, I), haloalkyl (such as $CCl_3$ or $CF_3$). Exemplary substituents also comprise one or more of the following groups: halo (such as F, $C_1$, Br, or I), haloalkyl (such as $CCl_3$ or $CF_3$), alkoxy, alkylthio, hydroxy, carboxy, carbonyl, epoxy, alkyloxycarbonyl, alkylcarbonyloxy, amino, carbamoyl, urea, alkylurea or thiol and additional groups identifiable by a skilled person upon reading of the present disclosure.

Accordingly, the term "substituted alkyl" refers to an alkyl moiety substituted with one or more substituent groups, Similarly, the term "substituted aryl" refers to an aryl moiety substituted with one or more substituent groups. For example substituted alkyl comprise aralkyl and substituted aryl comprise alkaryl compound or group. The term "aralkyl" as used herein refers to an alkyl group with an aryl substituent, and the term "alkaryl" as used herein refers to an aryl group with an alkyl substituent, wherein "aryl" and "alkyl" are as defined above. In some embodiments, alkaryl and aralkyl groups contain 6 to 12 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 3-ethylcyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, and the like. The terms "alkaryloxy" and "aralkyloxy" refer to substituents of the formula —OR wherein R is alkaryl or aralkyl, respectively, as defined.

As used herein the terms "heteroatom-containing" or "hetero-" indicated in connection with a group, refers to a hydrocarbon group in which one or more carbon atoms is replaced with an atom other than carbon, e.g., nitrogen, oxygen, sulfur, phosphorus or silicon. Exemplary "heteroatoms" comprise such as N, O, S, and P, and can be present in a compound by a covalent bond to each of two carbon atoms, thus interrupting the two carbon atoms. Accordingly, the term "heteroalkyl" refers to an alkyl substituent or group that is heteroatom-containing, the term "heterocyclic" refers to a cyclic substituent that is heteroatom-containing, the terms "heteroaryl" and "heteroaromatic" respectively refer to "aryl" and "aromatic" substituents or groups that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkyl ethers, secondary and tertiary alkyl amines, amides, alkyl sulfides, alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, and addition group identifiable by a skilled person.

Accordingly, the term "heteroatom-containing alkyl" and "heteroalkyl" refer to alkyl compounds or groups in which at least one carbon atom is replaced with a heteroatom, such as nitrogen, oxygen or sulfur. Similarly, the terms "heteroatom-containing aryl" and "heteroaryl" refer to aryl compounds or groups in which at least one carbon atom is replaced with a heteroatom, such as nitrogen, oxygen or sulfur.

The terms "cyclic", "cycle" and "ring" when referred to a group of atoms refer to alicyclic or aromatic groups that in some cases can be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic. Accordingly, the term "cycloalkyl" refers to a cyclic alkyl group, typically having 3 to 8, preferably 5 to 7, carbon atoms such as cyclohexyl group. "Heterocycloalkyl" refers to a saturated or partially saturated monocyclic, bicyclic, or polycyclic ring in which at least one carbon atom is replaced with a heteroatom selected from S, O, P and N, preferably from 1 to 3 heteroatoms in at least one ring.

Exemplary organic compounds or molecules comprising an aliphatic or aromatic group which can be target compounds in the sense of the disclosure comprise amino acids, mono and disaccharides, lipids such as cholesterol as well as more complex molecules such as proteins, fatty acids, phospholipids and polysaccharides as will be understood by a skilled person.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH$_2$) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In particular in some embodiments, a target compound can be a natural or unnatural aminoacids, derivative of natural aminoacids, oligopeptide and/or a protein. Exemplary aminoacid includes D or L-Alanine, D or L-Arginine, D or L-Asparagine, D or L-Aspartic acid, D or L-Cysteine, D or L-Glutamic acid, D or L-Glutamine, Glycine, D or L-Histidine, D or L-Isoleucine, D or L-Leucine, D or L-Lysine, D or L-Methionine, D or L-Phenylalanine, D or L-Proline, D or L-Serine, D or L-Threonine, D or L-Tryptophan, D or L-Tyrosine, and D or L-Valine.

The term saccharide as used herein indicates a biomolecule consisting of carbon (C), hydrogen (H) and oxygen (O) atoms, usually with a hydrogen-oxygen atom ratio of 2:1 with an empirical formula $C_m(H_2O)_n$ where m may be different from n. In some embodiments, a target compound can be a monosaccharide, disaccharide or a polysaccharide. Exemplary monosaccharides include glucose (dextrose), fructose (levulose), and galactose. Examples of disaccharides includes sucrose and lactose. Examples of polysaccharides includes cellulose and starch.

In some embodiment, the target compound can be a protein. The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. A polypeptide of at least two amino acids and up to 50 amino acids as used herein is defined as a peptide.

Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immuno precipitation, and a variety of other methods as understood by a person skilled in the art. Proteins can be provided in vitro or in vivo by several methods identifiable by a skilled person.

In some embodiment, the target compound can be a fatty acid. The term "fatty acid" as used herein refers to a carboxylic acid with a long aliphatic chain which is either saturated having no double or triple bonds or unsaturated having at least one double or triple bond. Typically having 4 or more carbon atoms and less than 30 carbon atoms and their modified derivatives. Example classes of fatty acids include ω-3, ω-6, ω-7, and ω-9. Exemplary fatty acids comprise arachidic acid, stearic acid, palmitic acid, erucic acid, oleic acid, linolenic acid, linoleic acid, and arachidonic acid. Exemplary material comprising fatty acids are lard, butter, coconut oil, sunflower oil, palm oil, cottonseed oil, soybean oil, olive oil, and corn oil.

In some embodiment, the target compound can be a phospholipid. Phospholipids are a subclass of fatty acid. Examples include docosahexaenoic acid (DHA), eicosapentaenoic acid (EPA), phosphatidic acid, phosphatidylethanolamine, phosphatidylcholine, phosphatidylserine, phosphoinositides, ceramide phosphorylcholine, ceramide phosphorylethanolamine, and ceramide phosphryllipid.

In some embodiment, the target compound can be a polysaccharide. The term "polysaccharide" as used herein indicates a polymeric carbohydrate molecule composed of long chains of monosaccharide units bound together by glycosidic linkages, and on hydrolysis give the constituent monosaccharides or oligosaccharides. Polysaccharide ranges in structure from linear to highly branched. Exemplary polysaccharide comprise starch, glycogen, cellulose, chitin, amylose, amylopectin, callose, laminarin, chrysolaminarin, xylan, arabinoxylan, mannan, fucoidan, and galactomannan.

In several embodiments herein described the target compounds can be or comprise impurities such as contaminants or remnants of previous physical or chemical reactions of the mixture which are either naturally occurring or added during synthesis of a chemical or commercial product. Impurities in the sense of the disclosure comprise any chemical substance that can be purposely, accidentally, inevitably, or incidentally added into the mixture.

For example, in some embodiment, the target compound can comprise a chaotropic agent selected from n-butanol, ethanol, guanidinium thiocyanate, guanidinium chloride, lithium perchlorate, lithium acetate, magnesium chloride, phenol, 2-propanol, sodium dodecyl sulfate, thiourea, and urea.

Similarly, in some embodiments, a target compound can comprise a buffer agent such as phosphate buffer saline, N-(2-Acetamido)-aminoethanesulfonic acid (ACES), Salt of acetic acid (Acetate), N-(2-Acetamido)-iminodiacetic acid (ADA), 2-Aminoethanesulfonic acid, Taurine (AES), Ammonia, 2-Amino-2-methyl-1-propanol (AMP), 2-Amino-2-methyl-1,3-propanediol, (Ammediol or AMPD), N-(1,1-Dimethyl-2-hydroxyethyl)-3-amino-2-hydroxypropanesulfonic acid (AMPSO), N,N-Bis-(2-hydroxyethyl)-2-aminoethanesulfonic acid (BES), Sodium Bicarbonate, N,N'-Bis(2-hydroxyethyl)-glycine (Bicine), [Bis-(2-hydroxyethyl)-imino]-tris-(hydroxymethylmethane) (BIS-Tris), 1,3-Bis[tris(hydroxymethyl)-methylamino]propane) (BIS-Tris-Propane), Boric acid, Dimethylarsinic acid (Cacodylate), 3-(Cyclohexylamino)-propanesulfonic acid (CAPS), 3-(Cyclohexylamino)-2-hydroxy-1-propanesulfonic acid (CAPSO), Sodium carbonate, Cyclohexylaminoethanesulfonic acid (CHES), Salt of citric acid (Citrate), 3-[N-Bis(hydroxyethyl)amino]-2-hydroxypropanesulfonic acid (DIPSO), Formate Salt of formic acid, Glycine, Glycylglycine, N-(2-Hydroxyethyl)-piperazine-N'-ethanesulfonic acid (HEPES), N-(2-Hydroxyethyl)-piperazine-N'-3-propanesulfonic acid (HEPPS, EPPS), N-(2-Hydroxyethyl)-piperazine-N'-2-hydroxypropanesulfonic acid (HEPPSO), Imidazole, Salt of malic acid (Malate), Maleate Salt of maleic acid, 2-(N-Morpholino)-ethanesulfonic acid (MES), 3-(N-Morpholino)-propanesulfonic acid (MOPS), 3-(N-Morpholino)-2-hydroxypropanesulfonic acid (MOPSO), Salt of phosphoric acid (Phosphate), Piperazine-N,N'-bis(2-ethanesulfonic acid) (PIPES), Piperazine-N,N'-bis(2-hydroxypropanesulfonic acid) (POPSO), Pyridine, Salt of succinic acid (Succinate), 3-{[Tris(hydroxymethyl)-methyl]-amino}-propanesulfonic acid (TAPS), 3-[N-Tris(hydroxymethyl)-methylamino]-2-hydroxypropanesulfonic acid (TAPSO), Triethanolamine (TEA), 2-[Tris(hydroxymethyl)-methylamino]-ethanesulfonic acid (TES), N-[Tris(hydroxymethyl)-methyl]-glycine (Tricine), and Tris(hydroxymethyl)-aminomethane (Tris).

In some embodiments, the target compound can comprise a constituent in a biological medium. An exemplary biological medium includes glucose, monobasic ammonium phosphate, sodium chloride, magnesium sulfate, and potassium phosphate. A further exemplary biological medium includes peptone, beef extract and agar lysogenic broth, yeast extract, blood agar, chocolate agar, and fastidious broth.

In some embodiments, a target compound can be a growth inhibitor to an organism such as gentian violet, bile salts, sodium desoxycholate to gram positive organism, potassium tellurite and sodium azide to a gram-negative organism, chloral hydrate and ethanol to a proteus.

In some embodiments, a target compound can be an antibiotic including but not limited to penicillin, streptomycin, cephalosporins, polymyxins rifamycins, lipiarmycins, quinolones, sulfonamides, macrolides, lincosamides tetracyclines, bactericidal aminoglycosides, cyclic lipopeptides (such as daptomycin), glycylcyclines (such as tigecycline), oxazolidinones (such as linezolid), and lipiarmycins (such as fidaxomicin), fluoroquinolones, or malachite green.

In embodiments herein described methods and systems of the instant disclosure separation of the mixture comprising the nucleic acid and the target compound is performed with a solid matrix.

The wording "solid matrix" as used herein indicates a solid material configured to retain the nucleic acid and the target compounds through the related sorption to the solid material. In particular, a solid material forming a solid matrix in the sense of the disclosure is configured to allow adsorption, and/or ion exchange of the nucleic acid or the target compound to the solid material. Exemplary solid matrix includes silica, polymer network or gel.

The term "adsorption" as used herein indicates adhesion of atoms, ions or molecules from a gas, liquid or dissolved solid to a surface [Ref.: "Glossary". The Brownfields and Land Revitalization Technology Support Center. Retrieved 2009 Dec. 21,] such as adhesion of a target compound to a surface of the solid material of the matrix. In particular, nucleic acids and/or target compound can adsorb to the matrix.

The term "ion exchange" as used herein indicates an exchange of ions between two electrolytes or between an electrolyte solution and a complex. In particular, in embodiments of the disclosure the solid material can be used as an "ion exchanger" which exchange positively charged ions (cations), negatively charged ions (anions) or both with the mixture under separation as will be understood by a skilled person.

In some embodiments, the solid material of the solid matrix herein described comprises silica, such as silica gel, including silicon spherical and irregular particle shape, as well as bare and modified/bonded silica products, in various grades, particle and pore sizes identifiable by a skilled person.

In particular in some embodiments, the silica material of the solid matrix can comprises a gel particle, glass particle, glass microfiber or slurry. In some embodiments, the glass particle can comprise a powder, microbead, silicate glass, flint glass, borosilicate glass, or glass fiber filter.

Binding of the nucleic acids and/or target compounds to the silica matrix can be performed through van der Waals forces (nonpolar interactions), dipole-dipole interactions (polar interactions), and hydrogen bonding. It is believed sodium ions play a role in facilitating the interactions between silica and the negatively charged oxygen on the nucleic acid's phosphate group. Without being bound by any specific theory, it is believed phosphate-silanol and hydrophobic interactions enable binding of nucleic acids to silica. Exemplary silica includes silica membranes, silica fibers, borosilicate glass fibers, borosilicate glass, borosilicate microfiber, and silica coated magnetic particles.

In some embodiments, the solid matrix comprises a solid material configured for ion exchange. In an ion exchange solid matrix, a cationic or anionic functional group is presented on the material forming the solid matrix. In the ion exchange solid matrix the cationic or anionic functional group is capable of electrostatic interaction with an ionic species of opposite charge. For example, an anionic exchange solid matrix is capable of electrostatically interacting with an ion of opposite charged species such as a nucleic acid.

In some embodiments, the anion exchange solid matrix comprises a cationic group represented by Formula (IV):

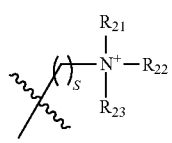

Formula (IV)

wherein
s is 1 to 6,
R21, R22, and R23 are independent selected from H, linear, branched, substituted or unsubstituted a lower alkyl group (C1-C4).

The anion functional group on the anion exchange resin or silica can be a tertiary or quaternary ammonium. An exemplary a tertiary ammonium can be a DEAE (diethylaminoethyl) wherein s is 2 and R21 and R22 are ethyl and R23 is a proton.

In some embodiments, the solid matrix comprises a resin, and s is 2 and R21 and R22 are ethyl groups and R23 is a proton.

Solid matrix comprising solid material configured for ion exchange can be unselective or have binding preferences for certain ions or classes of ions, depending on their chemical structure, depending on the size of the ions, their charge, or their structure. Typical examples of ions that can bind to ion exchangers are H+, OH−, singly charged inorganic ions like Na+, K+, and Cl−, doubly charged inorganic ions like Ca2+ and Mg2+, polyatomic inorganic ions like SO42− and PO43−, organic bases, usually molecules containing the amine functional group —NR2H+, organic acids, often molecules containing —COO— (carboxylic acid) functional groups and ionized organic molecules such amino acids, peptides, proteins and additional compound identifiable by a skilled person.

In some embodiments, the solid matrix has a cylindrical shape of a diameter ranging from 0.1 millimeter to 1 meter and a longitudinal dimension ranging from 0.1 millimeter to 1 meter.

In some embodiments, the solid matrix has a volume of 1 nanoliter to 1 L.

In some embodiments, the solid matrix can include silica in the form of gel particles, glass particles, glass fiber, glass microfibers or slurry resins, wherein the glass particles in turn can be be in the form of powder, microbeads, silicate glass, flint glass, borosilicate glass, or glass fiber filters.

In some embodiments, a solid matrix comprising glass fiber solid matrix can take the form of a packed column, or a packed filter configured for insertion within a microfluidic device, a packed filter configured for insertion in a centrifuge tube, or silica-coated magnetic particles in suspension.

In embodiments herein described methods and systems of the instant disclosure separation of a source mixture comprising target compound and a nucleic acid with a solid matrix are directed to separate the nucleic acid from one or more target compounds having a water solubility equal to or greater than 0.001 g per 100 mL.

The wording "solubility" as used herein indicates a chemical property referring to the ability for a chemical substance, the solute, to dissolve in a solvent. Accordingly, solubility is a measure of the amount of the solute that can dissolve in a solvent at a specific temperature. Accordingly, solubility is can be measured in terms of the maximum amount of solute dissolved in a solvent at equilibrium. Solubility can be measured in various units of concentration such as molarity, molality, mole fraction, mole ratio, mass (solute) per volume (solvent) and other units identifiable by a skilled person.

In particular, solubility of a first compound in a second compound can be measured by weighing a specific mass of the first compound and adding the second compound to the weighed specific mass of the first compound, in small increments. The mass at which the second compound does not dissolve into the first compound or does not form a homogeneous solution with the first compound is used to determine the solubility of the first compound in the second compound.

In some embodiments, methods and systems herein described are directed to selectively remove one or more target compounds having a water solubility equal to or greater than 0.001 g per 100 mL from a solid matrix further absorbing a nucleic acid. In those embodiments, selective removal of the target compound can be performed by contacting the solid matrix with a target compound removing agent having a water solubility equal to or less than 10 g per 100 mL with water having a solubility in the removing agent of less than 30 g per 100 mL, the contacting performed to remove the target compound from the solid matrix.

In particular, in methods herein described the contacting the solid matrix with a target compound removing agent comprises eluting the target compound from the solid matrix by washing the solid matrix with the target compound removing agent.

The wording "removing agent" as used herein indicates an organic compound having physico chemical properties allowing an interaction with a reference compound in the solid matrix in the sense of the disclosure, which results in the removal of the reference compound from the solid matrix.

In particular a removing agent capable of removing a target compound in the sense of the disclosure having a water solubility equal to or greater than 0.001 g per 100 mL typically refers to organic solvent comprising at least one organic compound which contains at least 5 carbons and has a water solubility equal to or less than 10 g per 100 mL of water with water having a solubility in the removing agent of less than 30 g per 100 mL at 25° C.

In some embodiments, the solubility in water of the removing agent selected to remove a target compound is equal to or less than 1 g per 100 mL, equal to or less than 0.1 g per 100 mL, equal to or less than 0.01 g per 100 mL, equal to or less than 0.001 g per 100 mL, equal to or less than 0.0001 g per 100 mL, at 25° C.

A skilled person will be able to identify a suitable removing agent based on the physico chemical properties of the target compound to be removed and the related attachment to the solid matrix.

In some embodiment, the target compound removing agent has a water solubility equal to or less than 1 g per 100 mL, equal to or less than 0.1 g per 100 mL, equal to or less than 0.01 g per 100 mL, equal to or less than 0.001 g per 100 mL, equal to or less than 0.0001 g per 100 mL at 25° C.

In preferred embodiments, a target compound removing agent to be used in methods and systems of the disclosure comprises removing agents having a water solubility from 0.01 mg/100 mL to 1 g/100 mL per 100 mL of water at 25° C. and more preferably from 0.1 mg/100 mL to 100 mg/100 mL per 100 mL of water at 25° C.

In some embodiment, the target compound removing agent is an organic compound of Formula (I):

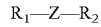  Formula (I)

wherein

Z is selected from the group consisting of $-(NR_{10})-$, $-O-$, $-S-$, $-(C=O)-$, $-CO_2-$, $-(CONR_{11})-$ and $-(OSiR_{12}R_{13}O)-$;

wherein

R1 is a linear, branched, substituted or unsubstituted alkyl, alkenyl, alkynyl group containing m number of carbons, wherein m is at least 1;

R2 is H or a linear, branched, substituted or unsubstituted alkyl, alkenyl, or alkynyl group containing n number of carbons, wherein n is at least 1;

wherein R10, R11, R12 and R13 are independently H, linear, or branched alkyl, alkenyl, or alkynyl group containing p number of carbons, wherein p is at least 1 and equal to or less than 4; and wherein a sum of m, n and p is at least 5.

In some embodiment, R10, R11, R12 and R13 can each independently be substituted with 0, 1, 2, 3 4, or at least 5 hydroxyl groups. In some embodiments, the target removing agent can be a mono alcohol, diol, or triol.

In some embodiment, in the removing agent of Formula (I)

Z is $-O-$, $-CO_2-$, or $-(CONR_{11})-$;

R1 is selected from the group consisting of a linear, branched, substituted or unsubstituted lower alkyl group, lower alkenyl group, lower alkynyl group, intermediate alkyl group, intermediate alkenyl group, intermediate alkynyl group, higher alkyl group, higher alkenyl group, and higher alkynyl group; and R2 is H.

A lower alkyl group as used herein contains 1 to 4 carbon atoms (C1-C4), such as methyl, ethyl, n-propyl, isopropyl, n-butyl, isobutyl, t-butyl, and the like, as well as cycloalkyl groups such as Cyclopropyl, cyclobutyl groups.

A lower alkenyl group as used herein contains 3 to 4 carbon atoms (C3-C4) and a C—C double bond, such as propenyl, butenyl, groups.

A lower alkynyl group as used herein contains 3 to 4 carbon atoms (C3-C4) and a C—C triple bond.

An intermediate alkyl group as used herein contains 5 to 7 carbon atoms (C5-C7), such as amyl, pentyl, hexyl, hepty and the like, as well as cycloalkyl groups such as cyclohexyl group.

An intermediate alkenyl group as used herein contains 5 to 7 carbon atoms (C5-C7) and at least one C—C double bond.

An intermediate alkynyl group as used herein contains 5 to 7 carbon atoms (C5-C7) and at least one C—C triple bond.

A higher alkyl group as used herein contains at least 8 carbon atoms, preferably 8 to 18 carbon atoms (C8-C18), such as n-octyl, n-nonyl, n-decyl, dodecyl, ricinoleyl, and the like, as well as cycloalkyl groups such as cyclooctyl group.

A higher alkenyl group as used herein contains at least 8 carbon atoms, preferably 8 to 18 carbon atoms (C8-C18), and at least one C—C double bond.

A higher alkynyl group as used herein contains at least 8 carbon atoms, preferably 8 to 18 carbon atoms (C8-C18), and at least one C—C triple bond.

In some embodiments, in the removing agent of Formula (I): Z is $-O-$; and R1 is 1-octyl, or 2-ethylhexyl.

In some embodiment, in the removing agent of Formula (I): Z is $-CO_2-$; and R1 is 1-octyl, 4-octyl or 2-ethylhexyl, or a combination thereof.

As used herein, a removing agent is defined as being "pH neutral" when upon contact with pure (pH=7) water in up to 1:1 mass ratio, they do not change the pH of the water by more than 2 units, 1 unit, more than 0.5 units, more than 0.2 units, more than 0.1 units. In some embodiments, a pH neutral removing agent has a water solubility equal to or less than 10 g per 100 mL.

In some embodiments the removing agent is selected from a group of compounds with water solubility, and such that upon contact with pure (pH=7) water in up to 1:1 mass ratio, they do not change the pH of the water by more than 1 unit, more than 0.5 units, more than 0.2 units, more than 0.1 units.

In some embodiments, a pH neutral removing agent has a water solubility equal to or less than 10 g per 100 mL.

In some embodiment, the target compound removing agent comprises substituted or unsubstituted linear or branched pH neutral alcohols having at least 6 carbon atoms, or at least 8 carbon atoms.

In some embodiment, the removing agent is selected from the group consisting of caprylic acid, capric acid, lauric acid, myristic acid, palmitic acid, or stearic acid, cis oleic acid, trans oleic acid, or a combination thereof.

In some embodiment, the removing agent is selected from the group consisting of myristoleic acid, palmitoleic acid, sapienic acid, oleic acids, elaidic acid, vaccenic acid, linoleic acid, linoelaidic acid, and α-linolenic acid, or a combination thereof.

In some embodiment, the removing agent is selected from the group consisting of palm oil, coconut oil, canola oil, soybean oil, sunflower oil, rapeseed oil, peanut oil, cotton seed oil, palm kernel oil, and olive oil, or a combination thereof.

In some embodiment, the removing agent is a silicone oil.

In some embodiment, the silicone oil comprises a compound having a linear or cyclic backbone represented by Formula (II):

$$E_1\text{-}[SiR_{14}R_{15}O]_h\text{-}E_2 \quad \text{Formula (II)}$$

wherein
R14 and R15 are independently linear, or branched, substituted or unsubstituted, alkyl, alkenyl, alkynyl, an aryl, alkylaryl containing h number of carbons, wherein h is at least 1 and equal to or less than 20;
E1 is selected from the group comprising null for cyclic backbone, H, OH, a lower alkyl group of C1-C4;
E2 is selected from the group comprising null for cyclic backbone, H, a lower alkyl, alenyl or alkynyl group of C1-C4; and
h is at least 1, 10, 30, 50 or 100.

In some embodiment, a silicone oil of Formula (II) can be decamethylcyclopentasiloxane having of Formula of $[(CH_3)_2SiO]_5$, wherein the silicone oil of Formula (II) has a cyclic backbone, and wherein E1 and E2 are null, and R14 and R15 are methyl groups, and h is 5.

In some embodiment, the removing agent is a silicone oil represented by Formula (III):

$$CH_3[Si(CH_3)_2O]_qSi(CH_3)_3 \quad \text{Formula (III)}$$

wherein q is at least 1, 10, 30, 50 or 100.

In some embodiments, the removing agent can be a silicone oil of Dow Corning Corporation 200® fluid from Dow Corning Corporation.

In preferred embodiments, target compounds removing agents selected to separate a nucleic acid from mixture of interest such as processed or unprocessed samples comprise the agents listed in Table 1 together with related solubility in water.

TABLE 1

| Removing agent | Water solubility at 25° C. |
|---|---|
| 1 butanol | 8 g/100 mL |
| 1 pentanol | 2.2 g/100 mL |
| 1 octanol | 0.03 g/100 mL |
| 1 nonanol | 0.013 g/100 mL |
| 5 nonanol | 0.046 g/100 mL |
| 1 decanol | 0.0037 g/100 mL |
| 1 dodecanol | 0.004 g/100 L |
| 1 tridecanol | practically insoluble (a solubility of 1 g per 10 L of solvent) |
| Arachidyl Alcohol (20 ol) | 0.151 ug/100 mL |

As indicated above skilled person will be able to identify a suitable removing agent based on the physico chemical properties of the target compound to be removed and the related attachment to the solid matrix.

Exemplary target compounds and corresponding removing agent comprise a wash buffer containing 70% ethanol which can be removed with 1-octanol, 4-octanol, 5-nonanol, 2-decanol, 2-dodecanol, silicone oil, FC-40, FC-70, and a lysed sample containing chaotropic lysis agents that can be removed with 1-octanol, 5-nonanol, 2-decanol, 2-dodecanol).

In some embodiments, a target compound comprising a wash buffer containing 100% ethanol can be removed with a removing agent selected from the group comprising 1-octanol, 4-octanol, 5-nonanol, 2-decanol, 2-dodecanol, silicone oil, FC-40, and FC-70 or any combination thereof.

In some embodiments, a target compound comprising a wash buffer containing 100% ethanol as can be removed with a removing agent selected from the group comprising 1-octanol, 4-octanol, 5-nonanol, 2-decanol, 2-dodecanol, silicone oil, FC-40, and FC-70 or any combination thereof, wherein the wash buffer containing 100% ethanol as a target compound is removed from a solid matrix selected from the group comprising Zymo-Spin™ IIC-XL Columns, Zymo-Spin I, Zymo-SpinIB, Zymo-Spin IC, Zymo-Spin IC-XL, Zymo-Spin II, Zymo-Spin IIC, Zymo-Spin IIN, Zymo-Spin V, Zymo-Spin VI, Zymo-Spin IIICG, Zymo-Spin IC-S, Zymo-Spin VI-P, Zymo-Spin V-E, Zymo-Spin III, QIAprep 2.0 Spin Miniprep Column, QIAamp Mini Spin Columns, MinElute Spin Columns, DNeasy Mini Spin Columns, RNeasy Mini Spin Columns, RNeasy MinElute Spin Columns, borosilicate Glass Fiber Grade A, borosilicate Glass Fiber Grade B, borosilicate Glass Fiber Grade C, borosilicate Glass Fiber Grade D, borosilicate Glass Fiber Grade E, borosilicate Glass Fiber Grade F, borosilicate Glass Fiber Grade 934-AH, borosilicate Glass Fiber Grade TSS, borosilicate Glass Fiber Grade VSS, and borosilicate glass capillaries.

In some embodiments, the target compound removing agent is selected to be hydrophilic enough to wet the solid matrix and solubilize target compounds such as salts, or ethanol or other contaminants, but hydrophobic enough to separate from water.

In some embodiments, the target compound removing agent is selected to physically displace a target compound originating from the sample, or from sample processing with agents (e.g. lysis buffer, wash buffer).

In some embodiments, the target compound removing agent is selected to be capable of solubilizing and removing a target compound originating from the sample.

In some embodiments, the target compound is selected to physically displace a target compound originating from the sample, or from processing the sample with agents such as silicone oil or FC-40 to displace lysis buffer or wash buffer containing ethanol.

In some embodiments, the target compound removing agent is selected to be capable of solubilizing and removing a target compound originating from the sample such as 1-octanol and wash buffer containing ethanol.

In some embodiments, the solid matrix has a solid matrix volume, the removing agent has a removing agent volume, the removing agent volume is 1 to 10 times or more the solid matrix volume; and the removing agent is eluted through the solid matrix at a flow rate of 1 microliter per second to 10 milliliter per second.

In some embodiments, the solid matrix has a solid matrix volume and the removing agent is eluted through the solid matrix under a pressure from 0.2 psi to 100 psi or from 1 psi to 10 psi.

In some embodiments, contacting the solid matrix with a target compound removing agent comprises eluting the removing agent through the solid matrix to remove at least 95%, 97%, 99%, 99.5%, 99.99%, or 99.999% of the target compound from the solid matrix.

In some embodiments, contacting the solid matrix with a removing agent is performed to obtain in a solid matrix retaining at least 10%, 20%, 30%, 50%, 75%, 90%, 95%, 98%, 99%, 99.5%, 99.8%, 99.9%, or 99.99% of the nucleic acid.

In some embodiments, the removing agent according to the disclosure can be used in alternative or in addition to additional removing agent such as an ethanol wash.

In some embodiments, removal of the target compound can be used in a method to capture a nucleic acid in a solid matrix. The term "capture" as used herein indicates the inhibition or prevention of chemical behavior of a compound by combination with added materials so that the captured compound is no longer available for reactions. In particular, in some embodiments of the disclosure, capturing of the nucleic acid is performed by sequestration of the nucleic acid by the solid matrix.

In those embodiments, the method comprises contacting the solid matrix with a solution comprising the nucleic acid together with a target compound having a water solubility equal to or greater than 0.001 g per 100 mL; and contacting the solid matrix with a target compound removing agent having a water solubility equal to or less than 10 g per 100 mL with water having a solubility in the removing agent of less than 30 g per 100 mL. In those embodiments, the contacting the solid matrix with a target compound removing agent is performed to remove the target compound from the solid matrix thus capturing the nucleic acid in the solid matrix.

In some of those embodiments, the captured nucleic acid is then removed from the solid matrix, by contacting the solid matrix with a nucleic acid removing agent. In particular, in methods herein described the contacting the solid matrix with a nucleic acid removing agent comprises eluting the nucleic acid from the solid matrix by washing the solid matrix with the nucleic acid removing agent.

In some of those embodiments, the nucleic acid removing agent can comprise nuclease-free water, preferably having a pH value within the range of pH 2 to 12, or within a range of pH 5 to 8. As used herein, a nuclease-free water is a substantially pure water (i.e. containing contains less than 100 ppm of dissolved or suspended material) that contains no detectable nuclease.

In some of those embodiments, a nucleic acid removing agent can comprise a Tris-EDTA Buffer, distilled water, a DNA Elution Buffer (e.g. Zymo Research, D3004-4-10), and DNase/RNase-Free Water (e.g. Zymo Research, W1001-1), or any combination thereof. In some of those embodiments, the nucleic acid removing agent or elution buffers can be heated to a temperature between 20° C. and 99° C.

In some embodiments, the nucleic acid removing agent is buffered to have a pH within the range of pH of 2 to 12, preferably have a pH value ranging from 3 to 10, from 4 to 9, from 5 to 8 or from 6 to 8. In some embodiments, the buffered nucleic acid removing agent contains Tris.

In some embodiments, the buffered nucleic acid removing agent contains EDTA. In some preferred embodiments, the buffered nucleic acid removing agent is a nuclease-free water buffered with Tris-EDTA. Accordingly, in some preferred embodiments, the nucleic acid removing agents comprise at least one of nuclease-free water, or Tris EDTA buffer.

In some embodiments, the eluted nucleic acids are single-stranded DNA, double-stranded DNA, single-stranded RNA, double-stranded RNA, plasmid DNA, short fragments less than 50 base pairs, short fragments between 50 and 150 base pairs, medium fragments between 150 base pairs to 3 kilobase pairs, long fragments greater than 3 kilobase pairs, genomic DNA, chromosomal DNA, mitochondrial RNA, ribosomal RNA, messenger RNA, transfer RNA, small nuclear RNA, synthesized DNA, or synthesized RNA In some embodiments, wherein the method is directed to elute nucleic acids other than DNA the method further comprises contacting the solid matrix with a DNAase prior to performing contacting the solid matrix with a nucleic acid removing agent. In some embodiments, wherein the method is directed to elute nucleic acids other than RNA the method further comprises contacting the solid matrix with a RNAase prior to performing contacting the solid matrix with a nucleic acid removing agent.

In some of those embodiments, the captured nucleic acid eluted from the solid matrix is used to perform a biochemical reaction of interest (target biochemical reaction) In those embodiments, the eluted nucleic agent is contacted with suitable reagents to perform the target biochemical reaction of the nucleic acid. Exemplary target biochemical reaction of the nucleic acid comprise nucleic acid amplifications such as polymerase chain reaction (PCR) or loop-mediated isothermal amplification (LAMP), strand displacement amplification, helicase-dependent amplification, nicking enzyme amplification reaction, sequencing, next-generation sequencing, nanopore sequencing, reverse transcription, quality analysis, ligation of sequencing barcodes, cloning, gel electrophoresis, cell-free extract transcription translation, plasmid generation, and CRISPR-Cas9, in-vitro transcription.

In some embodiments, the target biochemical reaction is LAMP. In those embodiments, the target compound removing agent is preferably 1-octanol 2 decanol, 2-dodecanol (see Example 2, Example 6 and Example 7), In some embodiments, the target biochemical reaction is PCR. In those embodiments, the target compound removing agent is preferably 1-octanol, 2-decanol, 2-dodecanol, 5 cst Silicone and Fc40 (see Example 5 and Example 7).

In some embodiment, the target biochemical reaction of the nucleic acid is DNA or RNA sequencing.

In some embodiment, the target biochemical reaction of the nucleic acid comprises ligation of sequencing barcodes.

In some embodiments, the target biochemical reaction of the nucleic acid is the ligation of sequencing barcodes to provide a mixture of another target compound and another nucleic acid. In those embodiments the mixture of another target compound and another nucleic acid can optionally be contacted by a second removing agent to capture another nucleic acid, wherein the another nucleic acid can be optionally used in another target biochemical reaction such as DNA or RNA sequencing.

In some embodiments, the target biochemical reaction is sanger sequencing, pyrosequencing, large-scale sequencing, next-generation sequencing, whole-genome sequencing, or nanopore sequencing.

In some embodiments, the target downstream reaction is sanger sequencing, pyrosequencing, large-scale sequencing, next-generation sequencing, whole-genome sequencing, or nanopore sequencing.

In those embodiments, contamination of target compounds or target compound removing agent into the elution can be disruptive to downstream analyses. Therefore, in those embodiments, the target compound removing agent is selected so that the selected removing agent inhibits a target enzyme catalyzing a target biochemical reaction of the nucleic acid by a rate of less than 50% when the target compound removing agent is comprised in the target compound removing agent at a concentration equal to or higher than 10% of a saturated concentration of the target compound removing agent in the nucleic acid removing agent.

In some of those embodiments, the inhibition of the rate of the target enzyme by the selected target compound removing agent is measured when the target compound removing agent is comprised in the nucleic acid removing agent at a concentration equal to or higher than 50% of the saturated concentration of the target compound removing agent in the nucleic acid removing agent.

In some of those embodiments, the inhibition of the rate of the target enzyme by the selected target compound removing agent is measured at the saturated concentration of the target compound removing agent in the nucleic acid removing agent.

In some of those embodiments, the target compound removing agent is selected to inhibit the target enzyme by a rate of less than 25%, more preferably less than 10% even most preferably less than 5%.

In some embodiments, the half or more of a saturated concentration of the target compound removing agent in the nucleic acid removing agent is 1 g per 100 mL.

In particular, in some embodiments a target removing agent with low solubility in water does not significantly inhibit PCR or LAMP efficiency and the PCR delay is less than 10 cycles, 9 cycles, 8 cycles down to 1 cycle, or the LAMP delay is less than 1 min, 2 min, 3 min, 4 min, 5 min, 10 min or 20 min and is thus less inhibitory than ethanol.

Exemplary target compound removing agents capable of inhibiting a target enzyme catalyzing a target biochemical reaction of the nucleic acid by a rate of less than 50% at 1 g per 100 mL, comprise 1-octanol as well as other long-chain alcohols such as 2-octanol, 4-octanol, nonanol, decanol, heptanol, hexanol, dodecanol, or molecules such as long carboxylic acids, isoamyl alcohol, or mixes of the molecules mentioned above with tetradecane, silicone oil or fluorocarbon oils. Exemplary fluorocarbon oil includes Fluorinert™ FC-40 manufactured by 3M Company having Corporate headquarters at 3M Center, St. Paul, Minn. 55144-1000. Exemplary silicone oil are the compounds of Formula (II) or Formula (III) of the instant disclosure.

In those embodiments, the elution comprising the nucleic acid can be used directly for the downstream target biochemical reaction, possibly in absence of dilutions which can be performed to dilute carryover contamination. In those embodiments, sequestered nucleic acids can provide a small fraction (<25%) or a larger fraction of the final nucleic acid amplification mixture. In preferred embodiments, the nucleic acid makes up a large fraction (50%-100% such as for lyophilized reagents) of the final nucleic acid amplification mix.

In those embodiments, the method of sequestration and washing a nuclei acid on a solid-phase column can comprises eluting the nucleic acid from the solid matrix with an approach including or not including centrifugation.

In an exemplary embodiment of an approach including centrifugation, the sample containing nucleic acids is mixed with a buffer such as a lysis buffer containing chaotropic salts. The lysed sample is centrifuged through a solid-phase column, such as a silica column, and the nucleic acids bind to the silica. A wash buffer, containing one or more target compound removing agents herein described, is centrifuged through the column to remove the chaotropic salts while maintaining the bond between the nucleic acids and silica. In some cases, two or three wash steps can be performed. In some cases, an additional dry centrifugation step can be performed. Water is then centrifuged through the column (elution step), which disrupts the bond between nucleic acids and silica, resuspending the nucleic acid into the aqueous solution.

In embodiments where contacting a solid matrix with a target compound removing agent in accordance with the disclosure comprises eluting the removing agent with centrifugation, preferred removing agents comprise 1-octanol, 2-decanol, 2-dodecanol 5 cst Silicon, and Fc40 (see Example 2, Example 5 and Example 6).

In other embodiments, methods and systems herein described can be used in non-centrifuge approaches to push solutions such as removing agents through the column when contamination of target compound is typically higher.

In an exemplary embodiment, a non-centrifuge approach comprises a pressure-based or vacuum-based pump fluidically connected to a column comprising a solid matrix.

In embodiments where contacting a removing agent is performed using pressure-based (positive-pressure or vacuum) pumping, air pushes liquid out of a few pores but the remaining pores can stay filled with liquid.

In embodiments where contacting a solid matrix with a target compound removing agent in accordance with the disclosure comprises eluting the removing agent without centrifugation (using pressure-based elution and in particular positive-pressure or vacuum elution), preferred removing agents comprise 1-octanol, 2 decanol and 2-dodecanol (see Example 7).

In particular these embodiments the use of removing agents such as 1-octanol and/or longer chain alcohols is especially beneficial as in centrifugation systems, contaminants can be removed more effectively when compared to pressurized systems, which are less effective in removing residual target compound. FIG. 1 demonstrates how the use of 1-octanol as an additional wash buffer improves loop-mediated isothermal amplification compared to an air-push through the solid phase column.

In both centrifugation and pressure-based pumping embodiments, a wash with a removing agent herein described can be performed alone or following contacting of the matrix with an ethanol wash or other wash. The purified nucleic acids with loop-mediated isothermal amplification (LAMP) can then be performed (see Examples 1-4).

In embodiments where the contacting of the solid matrix with the target compound removing agent is performed by eluting the solid matrix with a wash additional to an ethanol wash or other wash, preferred target compound removing agents comprise 1-octanol, 2-decanol, 2-dodecanol, 5 cst Silicone and Fc40 (see Example 5).

In embodiments where the contacting of the solid matrix with the target compound removing agent is performed by eluting the solid matrix with a wash replacing an ethanol wash or other wash, preferred target compound removing agents comprise 1-octanol, 2-decanol, 2-dodecanol, 5 cst Silicone and Fc40 (see Example 6).

In some embodiments, the solid-phase column is used for the selective capture of analytes, such as nucleic acids, in a process for purifying these molecules from a sample. In these purification protocols, the sample can be first mixed with chaotropic agents such as guanidinium thiocyanate, and this mixture is then pumped or centrifuged through the solid-phase column in order to capture nucleic acids on the column. Following this capture step, wash buffers comprising removing agent herein described can be used for removal of sample contaminants such as salts and proteins. Example samples typically comprise urine, blood, serum, plasma, and saliva.

In some embodiments of methods and systems herein described a target compound removing agent can be provided in the form selected from (a) partially miscible wash, (b) amphiphilic wash, and (c) partially miscible amphiphilic wash.

Partially miscible wash displaces previous washes and has low solubility in water of equal to or less than 10 g per 100 mL, equal to or less than 1 g per 100 mL, but equal to or higher than 0.01 microgram (μg) per 100 mL.

In some embodiments, partially miscible wash includes silicone oil, fluorinated oil as removing agent. In some embodiments, partially miscible wash is used in embodiments where the target compound removing agent is used an additional wash to remove ethanol.

An amphiphilic wash as used herein are polar enough to solubilize contaminants, salts, or wash buffer. Exemplary contaminants include lysis buffers containing chaotropic salts, wash buffers containing 60-80% ethanol, 100% ethanol. In some embodiments, amphiphilic wash comprises a removing agent in the form of ketones, alcohols, or carboxylic acids of C5-C7. In some embodiments, amphiphilic wash is used as a first wash in the NAs purification on a silica column to remove contaminants, salts.

A partially miscible amphiphilic wash indicates a wash comprising a removing agent that is polar enough to solubilize a target compound such as a contaminant but has low solubility in water of equal to or less than 10 g per 100 mL, equal to or less than 1 g per 100 mL, but equal to or higher than 0.01 microgram per 100 mL. The amphiphilic wash such 1-octanol and 2-decanol can interact better with the water-soluble contaminants than FC-40.

In some embodiments, a partially miscible amphiphilic wash is used as a first wash in the NAs purification on a silica column to remove contaminants, salts.

Exemplary partially miscible amphiphilic wash includes higher alcohols such as 1-octanol, octanol, nonanol, 5-nonanol, decanol, heptanol, hexanol, dodecanol, amyl alcohols, ricinoleyl alcohol or any combination thereof. Exemplary partially miscible amphiphilic wash also includes castor oil, linoleic acid, oleic acid, ricinoleic acid, stearic acid, palmitic acid, plant oils, vegetable oils, mineral oils or any combination thereof. Exemplary partially miscible amphiphilic washes further include one or more higher carboxylic acids. In some embodiments, a partially miscible amphiphilic wash can include any combination of 1-octanol, 2-octanol, 4-octanol, octanol, nonanol, 5-nonanol, decanol, heptanol, hexanol, dodecanol, amyl alcohols, ricinoleyl alcohol, castor oil, linoleic acid, oleic acid, ricinoleic acid, stearic acid, palmitic acid, plant oils, vegetable oils, mineral oils or one or more higher carboxylic acids.

In some embodiments, a target compound removing agent can be selected from the group consisting of palm oil, coconut oil, canola oil, soybean oil, sunflower oil, rapeseed oil, peanut oil, cotton seed oil, palm kernel oil and olive oil.

In some embodiments, one or more removing agent can be used for additional or replacement wash step in a solid-phase extraction (SPE) process wherein the solid matrix can include silica in the form of gel particles, glass particles, glass microfibers or slurry resins, wherein the glass particles in turn may be in the form of powder, microbeads, silicate glass, flint glass, borosilicate glass, or glass fiber filters.

In some embodiments, one or more target compound removing agents can be used for an additional or replacement wash step in a solid-phase extraction (SPE) process wherein the solid-phase can include diatomaceous earth, magnetic beads with complementary hybrids, anion exchange resins, or cellulose matrices.

In some embodiments, a target compound removing agent can be used for an additional or replacement wash step in a solid-phase extraction (SPE), wherein the solid-phase extraction (SPE) comprises normal phase SPE, reversed phase SPE, ion exchange SPE, or anion exchange SPE for targeted elution of a specific analyte or purification of a sample.

In some embodiments, a target compound removing agent can be used for an additional or replacement wash step in a solid-phase extraction (SPE) of a sample, wherein the sample includes urine, blood, serum, plasma, saliva, sputum, stool, cerebrospinal fluid (CSF), or resuspended swabs (nasal, throat, eye, ear, rectal, wounds, or vaginal, urethral).

In some embodiments, a target compound removing agent can be used for an additional or replacement wash step in a solid-phase extraction (SPE) of a sample, wherein the sample includes a cell culture.

In some embodiments, a target compound removing agent can be used for an additional or replacement wash step in a solid-phase extraction (SPE) of a sample, wherein the sample comprises an environmental sample including water, air, soil, or swab.

In some embodiments, a target compound removing agent can be used for an additional or replacement wash step in a solid-phase extraction (SPE) of a sample in food quality control, wherein the sample comprises grains, meat, seafood, plants, or fruits.

In some embodiments, a target compound removing agent can be used for an additional or replacement wash step in a solid-phase extraction (SPE) of a sample in water quality control, wherein the sample comprises water supply, tap water, agriculture water, beverages, milk, or juice.

In some embodiments, a target compound removing agent can be used for an additional or replacement wash step in a solid-phase extraction (SPE) of a sample of pharmaceutical.

In some embodiments, a target compound removing agent can be used for an additional or a replacement wash step in a solid-phase extraction (SPE) of a sample in biohazardous warfare testing.

In preferred embodiments the target compound to be removed comprises one or more non-nucleic acid compounds of mixtures such as processed or unprocessed: i) biological samples (e.g. urine, blood, serum, plasma, saliva), ii) environmental samples, ii) food samples, iv) cell cultures, v) water mixtures and vi) pharmaceutical mixtures. In particular in some of these preferred embodiments the mixture are processed with a buffer agent, such as a lysis buffer possibly containing chaotropic salts, and/or a wash buffer in particular when containing compounds such as ethanol (e.g. wash buffer containing over 60% ethanol), as well as additional buffer agents identifiably by a skilled person upon reading of the present disclosure.

In those preferred embodiments, preferred removing agents comprise agent having a water solubility from 0.01 mg/100 mL to 1 g/100 mL per 100 mL of water at 25° C. and more preferably from 0.1 mg/100 mL to 100 mg/100 mL per 100 mL of water at 25° C. In those embodiments, more preferred target compound removing agents comprise a removing agent of Table 1 or mixture thereof as will be understood by a skilled person upon reading of the present disclosure.

Typically, in those preferred embodiments the separation method is directed to separate the nucleic acid for preparation and/or analytical purposes.

In embodiments herein described, any one of the methods of the present disclosure can be performed with a corresponding system comprising a target compound removing agent having a water solubility equal to or less than 10 g per 100 mL with water having a solubility in the removing agent of less than 30 g per 100 mL; and at least one of a solid matrix configured to absorb a nucleic acid and a reagent to preform the biochemical reaction. In the system herein described the target compound removing agents, solid matrix and reagents are included in the system for simultaneous combined or sequential use in any one of the methods of the present disclosure. In some embodiments, the system can further comprise a nucleic acid removing agent as will be understood by skilled person.

The systems herein disclosed can be provided in the form of kits of parts. In kit of parts for performing any one of the methods herein described, the target compound removing agent, solid matrix, reagents to perform the target biochemical reaction and nucleic acid removing agent can be included in the kit alone or in the presence of one or more the reagents for the related detection and/or amplification such as probes for detection and/or amplification of an RNAs and/or corresponding cDNAs.

In particular, in some embodiment, a system comprises at least two of a target removing agent having a water solubility equal to or less than 10 g per 100 mL with water having a solubility in the removing agent of less than 30 g per 100 mL; the solid matrix configured to retain a nucleic acid. In some embodiment, the system can further comprise a nucleic acid removing agent.

In some embodiment, a system of the disclosure can contain a nucleic acid removing agent selected from nuclease-free water, distilled water, Tris EDTA buffer, Tris Buffer, DNA Elution Buffer (Zymo Research, D3004-4-10), DNase/RNase-Free Water (Zymo Research, W1001-1), Buffer EB (Qiagen, Cat No/ID: 19086).

In a kit of parts, the target compound removing agent, for example in a blister pack, solid matrix the reagents to perform biochemical reaction of interest such as LAMP or PCR the reagents for the related detection and additional reagents identifiable by a skilled person are comprised in the kit independently possibly included in a composition together with suitable vehicle carrier or auxiliary agents. For example, one or more removing agents can be included in one or more compositions together with reagents for detection of nucleic acid also in one or more suitable compositions.

Additional components can include labeled polynucleotides, labeled antibodies, labels, microfluidic chip, reference standards, and additional components identifiable by a skilled person upon reading of the present disclosure.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (i.e. wash buffers and the like).

Low toxicity, reactivity, health hazard to humans of removing agent allows broad use of removing agents herein descried in nucleic acid detection and/or amplification kits of the present disclosure.

Further details concerning the identification of the suitable carrier agent or auxiliary agent of the compositions, and generally manufacturing and packaging of the kit, can be identified by the person skilled in the art upon reading of the present disclosure.

In some embodiments, the method and systems of the disclosure can be used with a device such as the device described in U.S. application Ser. No. 16/130,810 filed on Sep. 13, 2018 and entitled "Purification and Detection of Analytes", incorporated herein by reference in its entirety. In those embodiments, a target compound removing agent can be stored in the system in foil or blister packs, which break at high pressures, or are pierceable by piercers on a pumping lid. For example, the pumping lid can have a sharp point which, when the lid is pushed down, will pierce the blister pack and release the target compound removing agent. The target compound removing agent within the blister is therefore free to exit the blister and enter the device's chamber. For example, the blister can be located within the chamber. In other embodiments, instead of a blister which envelops the target compound removing agent entirely, the target compound removing agent can be contained within the chamber, with a foil on the top of the chamber. In this case, the foil is pierced in a similar manner of the blister embodiment. The foil can also be on the bottom of the chamber, or both the top and bottom. The blister pack is essentially a foil which completely surrounds the target compound removing agent.

In some embodiments, the target compound removing agent can be collected in a storage or waste chamber after contacting the solid matrix.

In some embodiments, an amplification module containing at least one reaction well is provided. The eluted nucleic acids, for example, or other target analytes, can be inserted in parallel in each reaction well, enabling the parallel analysis of the same sample, with different reagents.

Embodiments of the methods and systems described herein can be performed with additional portable devices to accomplish the process of sequestration and washing of nucleic acid on solid matrix in a solid-phase column, and optionally additional target biochemical reaction with the nucleic acid so separated. In some embodiments, the portable device is a hand-held device.

Further details concerning the identification of the embodiments of methods and systems of the disclosure and related compositions, that can be performed in combination with such devices can be identified by the person skilled in the art upon reading of the present disclosure.

EXAMPLES

The methods and system herein disclosed are further illustrated in the following examples, which are provided by way of illustration and are not intended to be limiting.

The following material and methods were used in performing the experiments reported in the following examples.

LAMP Protocol:

LAMP reactions were carried out using standard conditions provided by NEB with slight modifications. LAMP solutions were provided by NEB unless otherwise noted. The final solution contained 1× Isothermal Amplification Buffer I, 1.4 mM dNTPs, 7 mM MgSO4 (5 mM+2 mM in buffer), WarmStart Bst 2.0 (320 U/mL), 1 mg/mL BSA (Ambion) Lambda phage LAMP primers (standard desalted, Integrated DNA Technologies) at concentrations 0.2 uM F3/B3, 1.6 uM FIP/BIP, 0.4 uM LoopF/B as previously developed by Goto in 2009 were used. For the detection of *Neisseria Gonorrhoeae*, in-house primers were developed and used at standard concentrations. Reactions were made to a total of 10 uL comprised of 9 uL concentrated reaction mix and 1 uL of template (purified nucleic acids) from the various extraction conditions. Where noted that a 2-fold dilution was used for LAMP reactions, 5 uL concentrated reaction mix and 5 uL of template were used instead. Each sample was tested in triplicate (n=3). The LAMP reaction was carried out by heating to 68° C. and all of the wells were tracked in real-time (image every 35 s) on the BioRad CFX-96 system. Samples were deemed negative and plotted with a time-to-positive of 0 min if they did amplify over a 30 min reaction. Cycle times were determined automatically using the BioRad analysis software and converted to time-to-positive in minutes.

ddPCR Protocol

Droplet digital polymerase chain reactions were carried out on a QX200™ Droplet Digital™ PCR System (BioRad, 2000 Alfred Nobel Drive Hercules, Calif. 94547). To obtain a more accurate value for the nucleic acid concentration, template was intentionally diluted 1 in 100 (reducing inhibitor concentration) into the final reaction mix. The final reaction mix contained 1× BioRad EvaGreen ddPCR Mix, 0.5 uM forward primer, 0.5 uM backward primer, and template. 22 uL of each sample and 65 uL QX200 droplet generation oil for EvaGreen was added to a DG8 cartridge. Each sample was tested in duplicate (n=2). A DG8 gasket was placed on top and using a DG8 cartridge holder, the chip was placed into the QX200 droplet generator. After droplet formation, droplets were transferred from the chip to a column of a 96-well plate, sealed with a heat-sealing foil, and thermocycled with the following settings: Initial denaturation (95 C for 3 min) and 40× cycles of denaturation (95 C for 30 s), annealing (60 C for 30 s), and elongation (68 C for 30 s). Droplets were stabilized by reducing the temperature to 4 C for 5 min followed by 90 C for 5 min and an infinite hold at 12 C until the samples were removed from the thermocycler. Droplets were analyzed on the QX200 droplet reader and a threshold manually determined where there was good separation between positive and negative droplets. Concentrations were calculated automatically by the software and normalized to the concentration of the positive control.

Example 1: Modified Protocol for ZR Viral DNA/RNA Kit

A modified protocol for running a ZR Viral DNA/RNA kit obtained from Zymo Research having a headquarter at 17062 Murphy Ave. Irvine, Calif. 92614, U.S.A. with a 5 mL syringe was tested with either an additional octanol step or dry push step. *Neisseria Gonorrhoeae* (NG) infectious stock from Zeptometrix having a headquarter at 878 Main Street, Buffalo, N.Y. 14202, U.S.A. was spiked into urine to a final concentration of 5000 CFU/mL. This solution was mixed 1:1 with DNA/RNA Shield™ (Zymo Research) and the combined solution was mixed with 2 volumes of Viral DNA/RNA lysis buffer (SKU D7020-1-100, Zymo Research).

750 uL of the lysed sample was added to a column and pushed through with a 5 mL syringe followed by another 750 uL lysed sample. Custom 3D printed adapters were made to attach the syringe to the Zymo-Spin™ IIC-XL Columns (Zymo Research). 1000 uL Viral wash buffer (Zymo Research) was added to the column and pushed through. Either 300 uL 1-octanol no solution was added to the column and pushed through with the 5 mL syringe. Lastly, 150 uL elution buffer was added and the final purified nucleic acid mix was obtained. A standard LAMP reaction with slight modifications was performed (NEB protocol). Primers were specific to NG and a larger template volume of 5 uL was used to highlight the effect of contaminants from the purified nucleic acid mix.

FIG. 1 shows results of nucleic acid amplification curves for loop-mediated isothermal amplification (LAMP) in a format where liquid solutions are pumped through the solid-phase silica purification columns by means of pressurization at 5 PSI of positive pressure. In the case where an ethanol-based wash buffer is performed followed by drying of the column with air pressurized at 5 PSI, the reaction starts amplifying target molecules at 22 min, whereas when using an additional wash based on 1-octanol, the reaction starts amplifying at 10 min.

Example 2: Nucleic Acid Extraction Comparative Study

A 500 mg/mL solution of purified lambda phage DNA (New England Biolabs, NEB, having 240 County Road, Ipswich, Mass. 01938) was spiked into molecular biology grade phosphate buffered saline (PBS from Corning, having corporate headquarter at one riverfront plaza, Corning, N.Y. 14831) to a final concentration of 5 mg/mL. This solution was extracted with either a ZR Viral DNA/RNA kit (Zymo 1), Quick-DNA/RNA Viral kit (Zymo 2), or a modified Zymo 1 protocol which comprises Zymo 1 protocol with an additional 1-octanol wash.

For all those three (3) conditions, lambda phage DNA in PBS was mixed 1:1 with a 2× solution of DNA/RNA Shield™ (Zymo Research). The resulting mixture was combined with 2 volumes of Viral DNA/RNA lysis buffer (Zymo Research, SKU D7020-1-100) and 500 uL of the combined mixture was added to the column. Centrifugations were performed at 16,000 xg, washing with viral wash buffer (Zymo Research) and ethanol (200-proof, Koptec, Decon Laboratories, Inc. 460 Glennie Circle King of Prussia, Pa. 19406) followed the respective Zymo protocols, and the elution volume was 50 uL. The extra octanol wash was added between the viral wash buffer and elution steps (500 uL, 2 min centrifugation). The 1-octanol was allowed to separate from the aqueous phase and only the aqueous phase was extracted for use in LAMP reactions.

For syringe pressure experiments, all centrifugation steps were replaced using a 5 mL luer-lok tip syringe (Becton Dickinson). ½" TFE tape was wrapped around the tip to ensure a tight seal with the Zymo-Spin™ IIC-XL Columns (Zymo Research). 500 uL of either lysed sample from the Zymo 1 protocol or modified Zymo 1 protocol viral wash buffer (Zymo Research), ethanol, 1-octanol (Sigma-Aldrich) were drawn into the 5 mL syringe. The syringe was drawn up to the 5 mL marking, connected to the column, and the syringe was pushed to the 3 mL marking and held in place until solution no longer flowed through the column). For the final step, 50 uL DNase/RNase-Free Water (Zymo Research) was used for the elution and purified nucleic acids were obtained.

Figure 2:
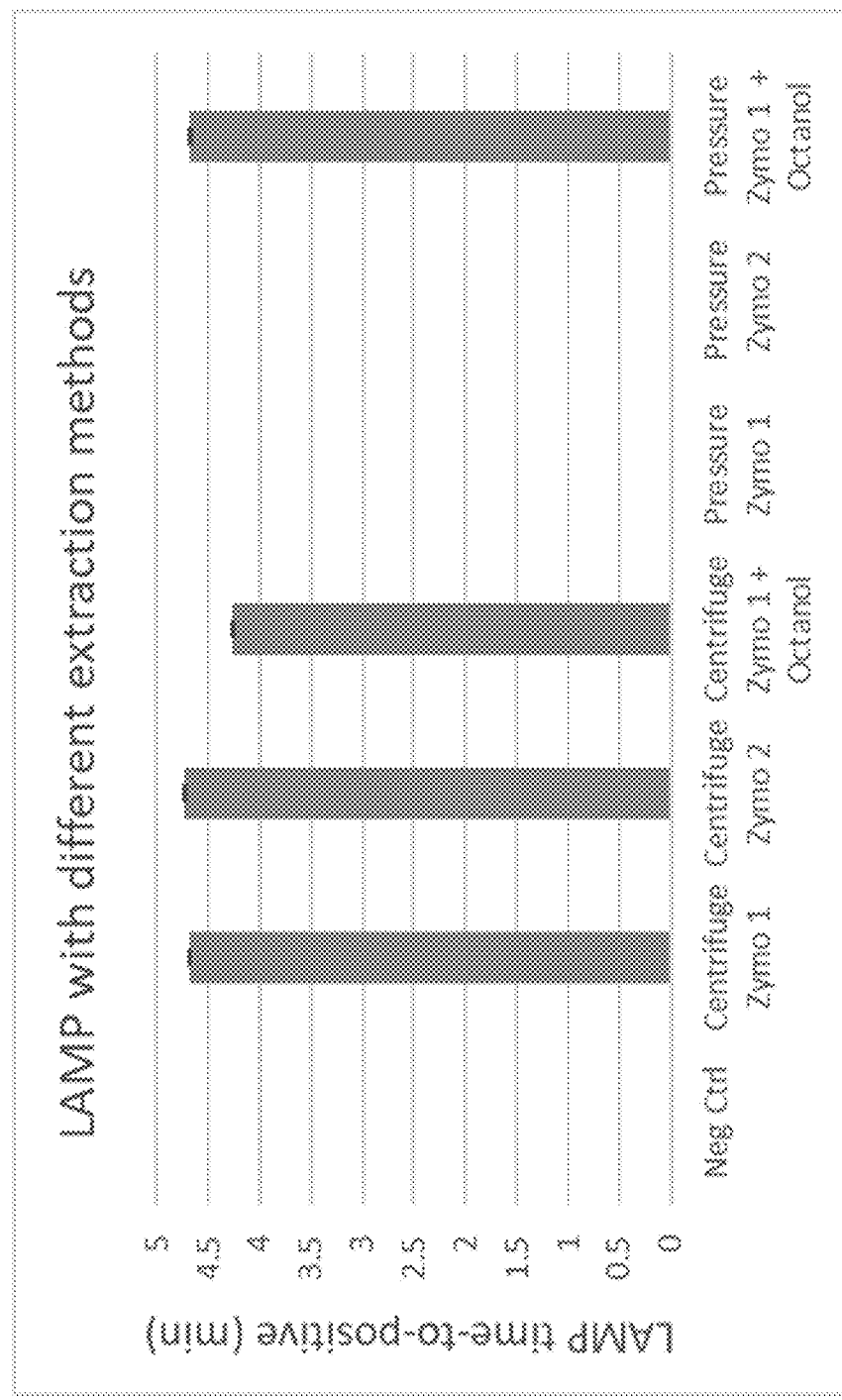
FIG. 2 shows a chart illustrating results of LAMP reactions performed on lambda phage DNA spiked in PBS and extracted through different methods as indicated. In the chart of FIG. 2, the LAMP amplification is expressed in time-to-positive values in minutes wherein time-to-positive of 0 min indicates that there was no amplification for at least 30 min. In the chart of FIG. 2, error bars represent the standard deviation for n=3.

FIG. 2 shows values of time-to-positive in minutes for LAMP reactions on lambda phage DNA spiked in PBS and extracted through different methods. Syringe pressure to push reagents through the column was compared to standard centrifugation. Conditions compare the Zymo ZR Viral DNA/RNA kit vs. Zymo Quick-DNA/RNA Viral kit vs. Zymo ZR Viral DNA/RNA kit with an additional octanol wash. Time-to-positive of 0 min indicates that there was no amplification for at least 30 min. Error bars represent the standard deviation for n=3.

Additional 1-octanol (Sigma-aldrich, 1-octanol for HPLC>99% purity) wash with centrifugation improves (i.e. reduces) LAMP ttp by 0.5 min.

Therefore, with additional step of 1-octanol wash, the 1-octanol pushes out the viral wash buffer of the column. The resulting elution contains 1-octanol carryover, but the bottom aqueous phase can be easily separated for downstream processing. Accurate LAMP detection is recovered using this method.

In contrast, using syringe air pressure allows too much carryover of the ethanol-based wash buffers which inhibits LAMP entirely.

Example 3: Loop Mediated Isothermal Amplification (LAMP

LAMP reactions were carried out using standard conditions provided by NEB with slight modifications. LAMP solutions were provided by NEB unless otherwise noted. The final solution contained 1× Isothermal Amplification Buffer I, 1.4 mM dNTPs, 7 mM MgSO4 (5 mM+2 mM in buffer), WarmStart Bst 2.0 (320 U/mL), 1 mg/mL BSA (Ambion) Lambda phage LAMP primers (standard desalted, Integrated DNA Technologies) at concentrations 0.2 uM F3/B3, 1.6 uM FIP/BIP, 0.4 uM LoopF/B as previously developed by Goto in 2009 were used. Reactions were made to a total of 10 uL comprised of 5 uL concentrated reaction mix and 5 uL of purified nucleic acids from the various extraction conditions (NF—H2O for negative control). For positive controls, 5 uL purified lambda phage DNA (5 mg/mL) was added to each reaction and for 5 uL template from nucleic acid extractions or each sample was tested in triplicate (n=3) and solutions were made to either 9 uL or 10 uL. The LAMP reaction was carried out by heating to 68° C. and all of the wells were tracked in real-time (image every 35 s) on the BioRad CFX-96 system. Samples were deemed negative if they did amplify over 30 min. Cycle times were determined automatically using the BioRad analysis software and converted to time-to-positive in minutes.

Example 4: LAMP with Contaminants

LAMP reactions were carried out in a similar fashion as in Example 3 but using 4 uL concentrated reaction mix, 5 uL purified lambda phage DNA (5 mg/mL, NEB), and 1 uL reserved for testing various conditions. See Table 2 for more details:

TABLE 2

LAMP with contaminants composition

| Condition | Reaction mix | Template | Additives |
|---|---|---|---|
| 10 uL (−) | 4 uL | 5 uL NF—H2O | 1 uL NF-H2O |
| 10 uL (+) | 4 uL | 5 uL 5 mg/mL λ, phage DNA | 1 uL NF-H2O |
| 10 uL (+), Viral Wash Buffer | 4 uL | 5 uL 5 mg/mL λ, phage DNA | 1 uL Viral Wash Buffer |
| 10 uL (+), Ethanol | 4 uL | 5 uL 5 mg/mL λ, phage DNA | 1 uL Ethanol |
| 10 uL (+), Octanol | 4 uL | 5 uL 5 mg/mL λ, phage DNA | 1 uL Octanol |
| 9 uL (+) | 4 uL | 5 uL 5 mg/mL λ, phage DNA | |

A typical LAMP reaction is made to 10 uL. The positive contains λ phage DNA whereas this volume was replaced with NF—H2O for the negative. For all of the "10 uL" conditions, 1 uL of 1 NF—H2O was replaced with 1 uL of either Viral Wash Buffer, Ethanol, or Octanol. Due to the low miscibility of octanol in water, the octanol separates from the bulk solution and forms a second phase on top. To check that the delay is due to the presence of octanol and not the about 10% change in LAMP reactant concentrations, a more concentrated positive control was made to only 9 uL.

Figure 3:
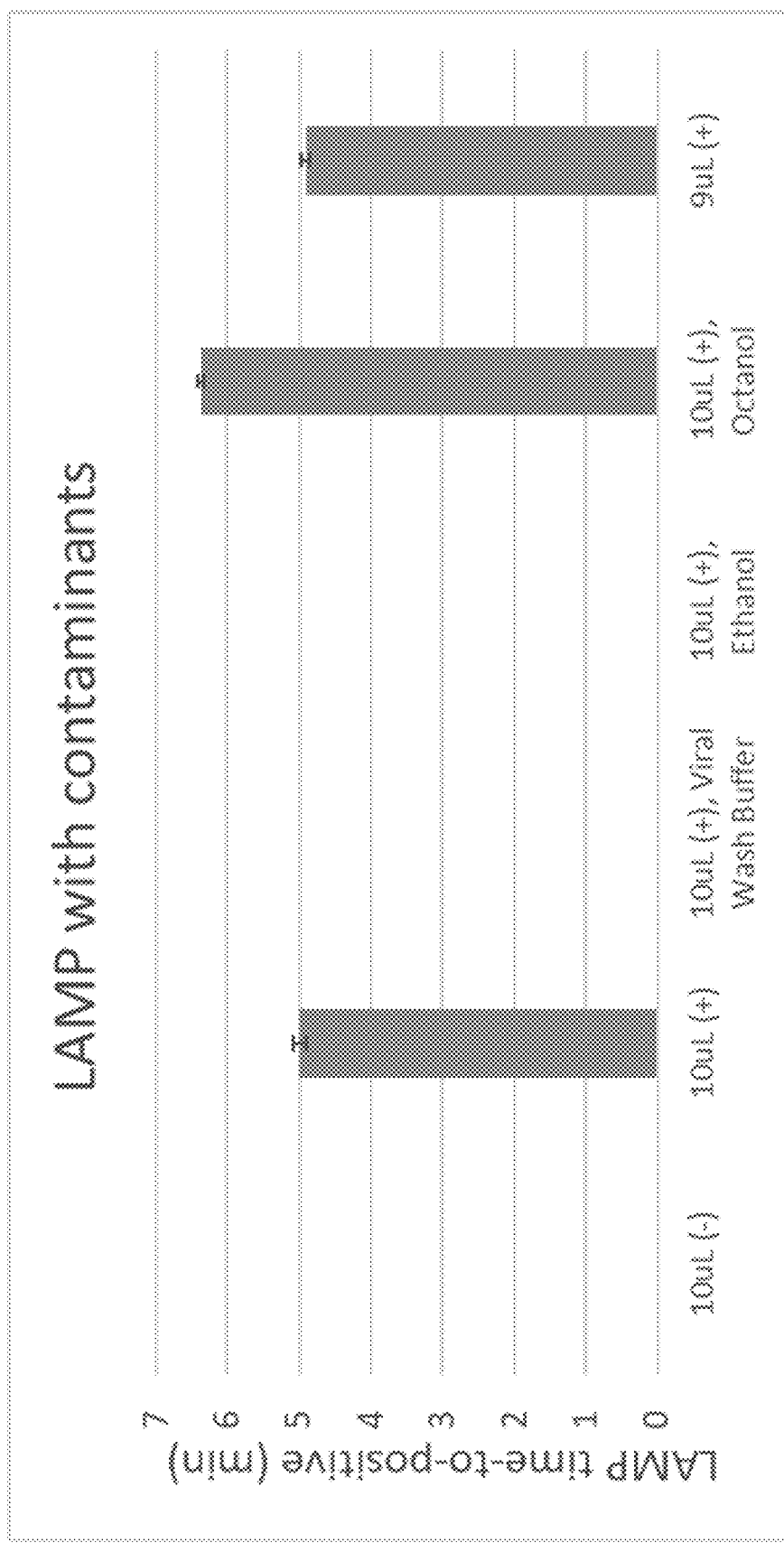
FIG. 3 shows a chart illustrating results of LAMP reactions performed on a volume of lambda phage DNA with or without additional compounds (Viral Wash Buffer, Ethanol or Octanol) or on a control as indicated in the figure. In particular, in the chart of FIG. 3, presence of the lambda phage DNA is indicated by (+) and absence of lambda phage DNA is indicated by (−). In the chart of FIG. 3, the LAMP amplification is expressed in time-to-positive values in minutes wherein time-to-positive of 0 min indicates that there was no amplification for at least 30 min. In the chart of FIG. 3, error bars represent the standard deviation for n=3.

FIG. 3 shows values of time-to-positive in minutes for LAMP reactions with spiked lambda phage DNA. (n=3) contaminants which may inhibit LAMP or affect the concentration of the solution are added. Time-to-positive of 0 min indicates that there was no amplification for at least 30 min. Error bars represent the standard deviation for n=3.

As used herein, "9 uL pos control" is 10% more concentrated LAMP mix but shows negligible difference from our standard 10 uL pos ctrl.

The result shows that 10% viral wash buffer or 10% ethanol completely inhibits the LAMP reaction. This represents 5 uL carryover in a 50 uL elution volume.

In contrast, 10% 1-octanol causes a 1.4 min delay in LAMP, but still provides accurate detection. However, a 2-phase extraction provides less than 10% n-octanol. When an eluted sample contains 10% 1-octanol, the octanol concentration can be further reduced using a syringe to extract the aqueous phase such that less than 1% octanol remains in the extracted solution.

Example 5: Centrifugation and Additional Wash

A 500 mg/mL solution of purified lambda phage DNA (New England Biolabs, NEB, having 240 County Road, Ipswich, Mass. 01938) was spiked into molecular biology grade phosphate buffered saline (PBS from Corning, having corporate headquarter at one riverfront plaza, Corning, N.Y. 14831) to a final concentration of 5 mg/mL.

This solution was extracted with either a ZR Viral DNA/RNA kit (Zymo 1 Pos Ctrl, Zymo Research, 17062 Murphy Ave. Irvine, Calif. 92614, U.S.A.), Quick-DNA/RNA Viral kit (Zymo 2), or a modified Zymo 1 protocol which comprises Zymo 1 protocol with an additional extra dry spin or wash step with 300 uL of either 100% ethanol, 1-octanol (Sigma-Aldrich, for HPLC, >99%, 293245), 5-nonanol (Sigma-Aldrich, >95% GC, 74310), 2-decanol (Sigma-Aldrich, 98% 118311), 2-dodecanol (Sigma-Aldrich, 99%, D221503), 5 cSt silicone oil, or FC-40.

The negative control condition was PBS without DNA and extracted with the same ZR Viral DNA/RNA kit. For all conditions, the PBS was mixed 1:1 with a 2× solution of DNA/RNA Shield™ (Zymo Research). The resulting mixture was combined with 2 volumes of Viral DNA/RNA lysis buffer (Zymo Research, SKU D7020-1-100) and 500 uL of the combined mixture was added to the column.

Centrifugations were performed at 16,000 xg, washing with viral wash buffer (Zymo Research) and ethanol (200-proof, Koptec, Decon Laboratories, Inc. 460 Glennie Circle King of Prussia, Pa. 19406) followed the respective Zymo protocols, and the elution volume was 50 uL. The extra wash was added between the viral wash buffer and elution steps. Following the elution, the tubes were vortexed and when applicable, the solution was allowed time to separate. The aqueous phase was carefully pipetted, and the template diluted 2-fold for each LAMP reaction and 100-fold for each ddPCR reaction.

Figure 4:
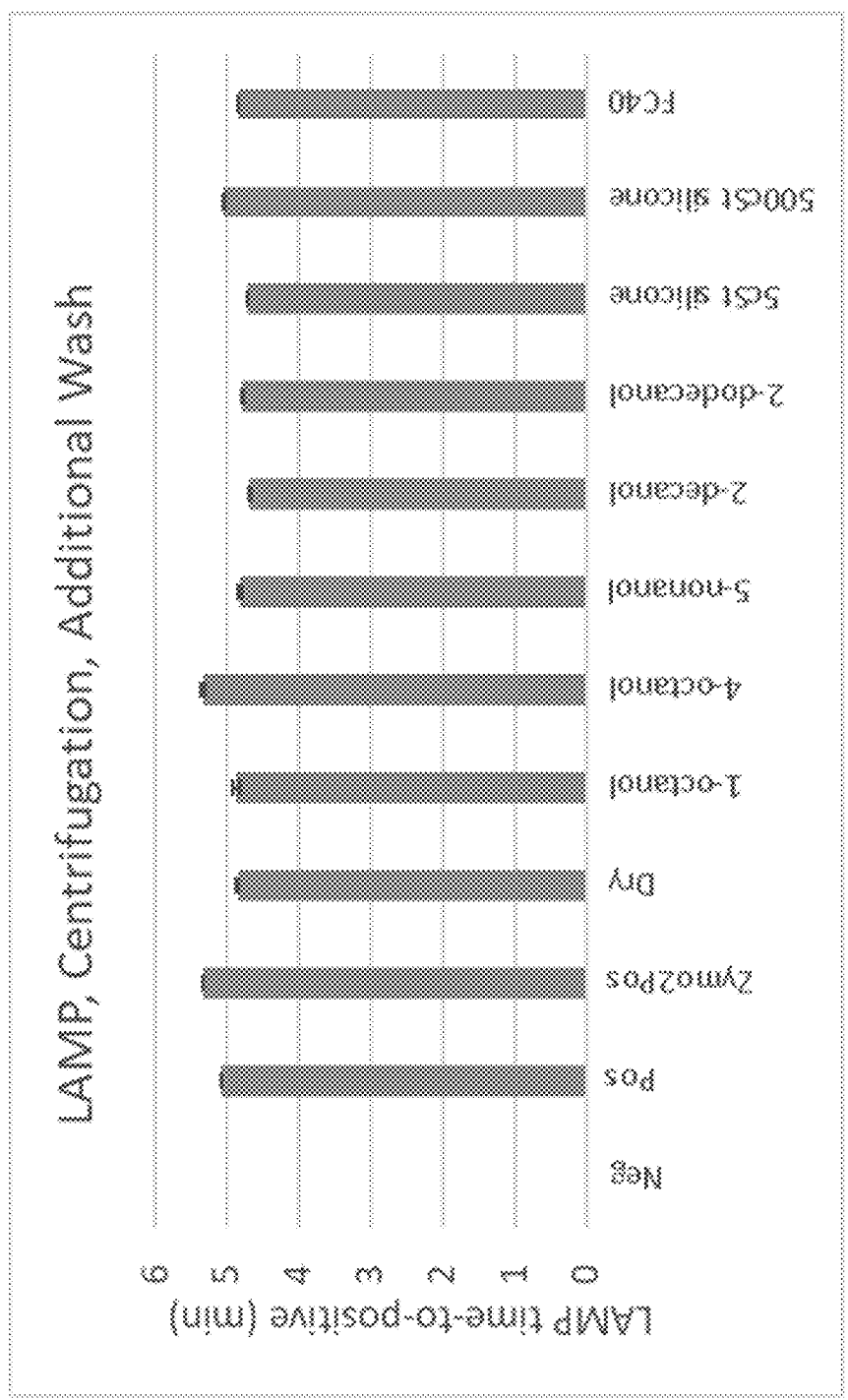
FIG. 4 shows a chart illustrating the results of LAMP reactions performed on lambda phage DNA spiked in PBS, extracted with centrifugation using ZR Viral DNA/RNA kit Zymo 1 (Pos), Quick-DNA/RNA Viral kit (Zymo2pos) or with a modified Zymo 1 with an additional extra dry spin (Dry) or wash step with ethanol, 1-octanol, 5-nonanol, 2-decanol, 2-dodecanol, 5 cSt silicone oil, or FC-40 as indicated. In the chart of FIG. 4, the LAMP amplification is expressed in time-to-positive values in minutes wherein time-to-positive of 0 min indicates that there was no amplification for at least 30 min. In the chart of FIG. 4, error bars represent the standard deviation for n=3.
Figure 5:
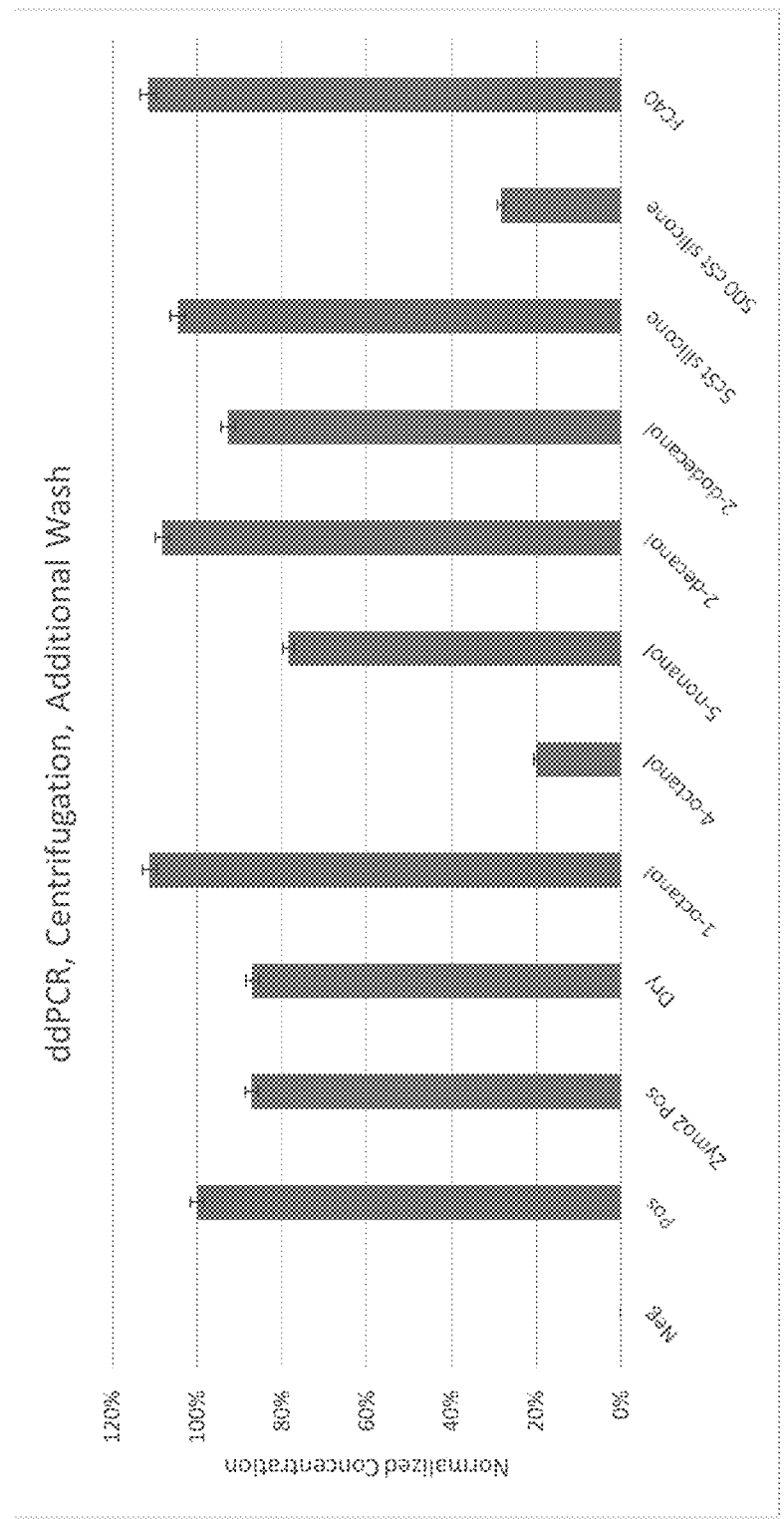
FIG. 5 shows a chart illustrating the results of digital PCR (ddPCR) reactions performed on lambda phage DNA spiked in PBS, extracted with centrifugation using ZR Viral DNA/RNA kit Zymo 1 (Pos), Quick-DNA/RNA Viral kit (Zymo2pos) or with a modified Zymo 1 with an additional extra dry spin (Dry) or wash step with ethanol, 1-octanol, 5-nonanol, 2-decanol, 2-dodecanol, 5 cSt silicone oil, or FC-40 as indicated. In the chart of FIG. 5, the results of the digital PCR amplification is expressed in normalized concentration. In the chart of FIG. 5, error bars represent the standard deviation for n=3.

The results illustrated in FIGS. 4 and 5 show the impact on LAMP reaction and ddPCR reaction of uses of an additional wash in a procedure comprising centrifugation (which has a low carryover).

In particular FIG. 4 shows the results of the LAMP reaction long-chain alcohols, silicone oil, and FC40 can be used as an additional wash after the viral wash buffer (70% ethanol). Dry, 1-octanol, 5-nonanol, 2-decanol, 2-dodecanol, 5 cSt silicone, and FC40 time to positive is slightly improved compared to the Pos control. In particular the LAMP results illustrated in FIG. 4 suggest that an additional dry spin or additional wash with 1-octanol, 5-nonanol, 2-decanol, 2-dodecanol, 5 cSt silicone oil, and FC-40 oil may be beneficial for improving LAMP time-to-positive. Without being bound by theory, it is believed that these washes are able to displace any remaining viral wash buffer in the column. After the elution, the template can be further purified from these additional wash buffers in a 2-phase extraction by pipetting selectively from the aqueous layer.

The data illustrated in FIG. 5 support the conclusion that with droplet digital PCR (ddPCR) the extraction efficiency is sufficient for all tested compounds except for 4-octanol and 500 cSt silicone oil.

Example 6: Centrifugation and Replacement Wash

A 500 mg/mL solution of purified lambda phage DNA (New England Biolabs, NEB, having 240 County Road, Ipswich, Mass. 01938) was spiked into molecular biology grade phosphate buffered saline (PBS from Corning, having corporate headquarter at one riverfront plaza, Corning, N.Y. 14831) to a final concentration of 5 mg/mL.

This solution was extracted with ZR Viral DNA/RNA kit (Pos) or a modified protocol in which the Viral Wash Buffer step was substituted with 500 uL 100% ethanol, 1-octanol, 5-nonanol, 2-decanol, 2-dodecanol, 5 cSt silicone oil, FC-40, or no wash. The negative control condition was PBS without DNA and extracted with the same ZR Viral DNA/RNA kit. For all conditions, the PBS was mixed 1:1 with a 2× solution of DNA/RNA Shield™ (Zymo Research).

The resulting mixture was combined with 2 volumes of Viral DNA/RNA lysis buffer (Zymo Research, SKU D7020-1-100) and 500 uL of the combined mixture was added to the column. Centrifugations were performed at 16,000 xg, washing with viral wash buffer (Zymo Research) and ethanol (200-proof, Koptec, Decon Laboratories, Inc. 460 Glennie Circle King of Prussia, Pa. 19406) followed the respective Zymo protocols, and the elution volume was 50 uL. Following the elution, the tubes were vortexed and when applicable, the solution was allowed time to separate. The aqueous phase was carefully pipetted, and the template diluted 2-fold for each LAMP reaction and 100-fold for each ddPCR reaction.

Figure 6:
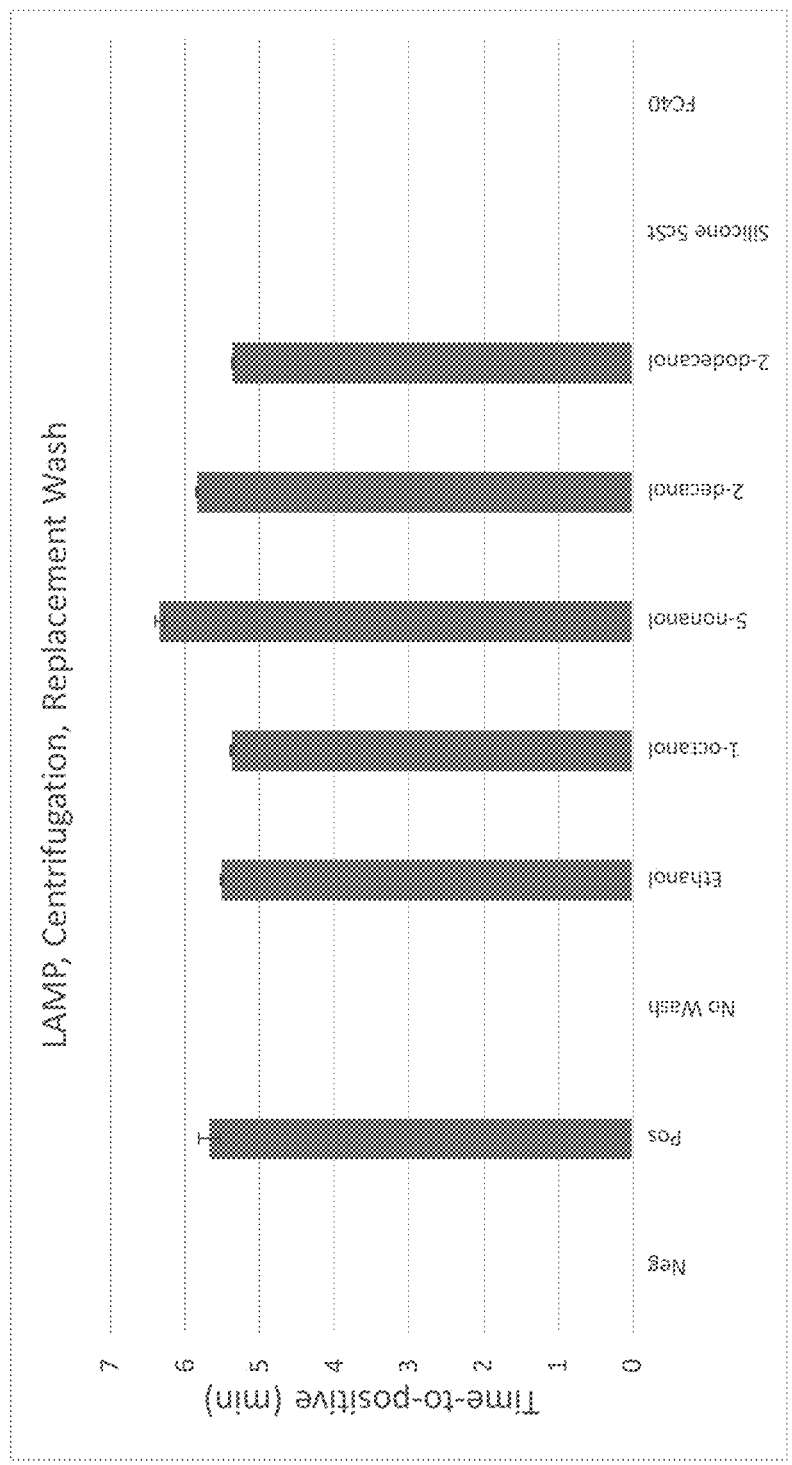
FIG. 6 shows a chart illustrating the results of LAMP reactions performed on lambda phage DNA spiked in PBS, extracted with centrifugation using ZR Viral DNA/RNA kit (Pos), or with a modified protocol with a wash step with ethanol, 1-octanol, 5-nonanol, 2-decanol, 2-dodecanol, 5 cSt silicone oil, or FC-40, or no wash step as indicated. In the chart of FIG. 6, the LAMP amplification is expressed in time-to-positive values in minutes wherein time-to-positive of 0 min indicates that there was no amplification for at least 30 min. In the chart of FIG. 6, error bars represent the standard deviation for n=3.
Figure 7:
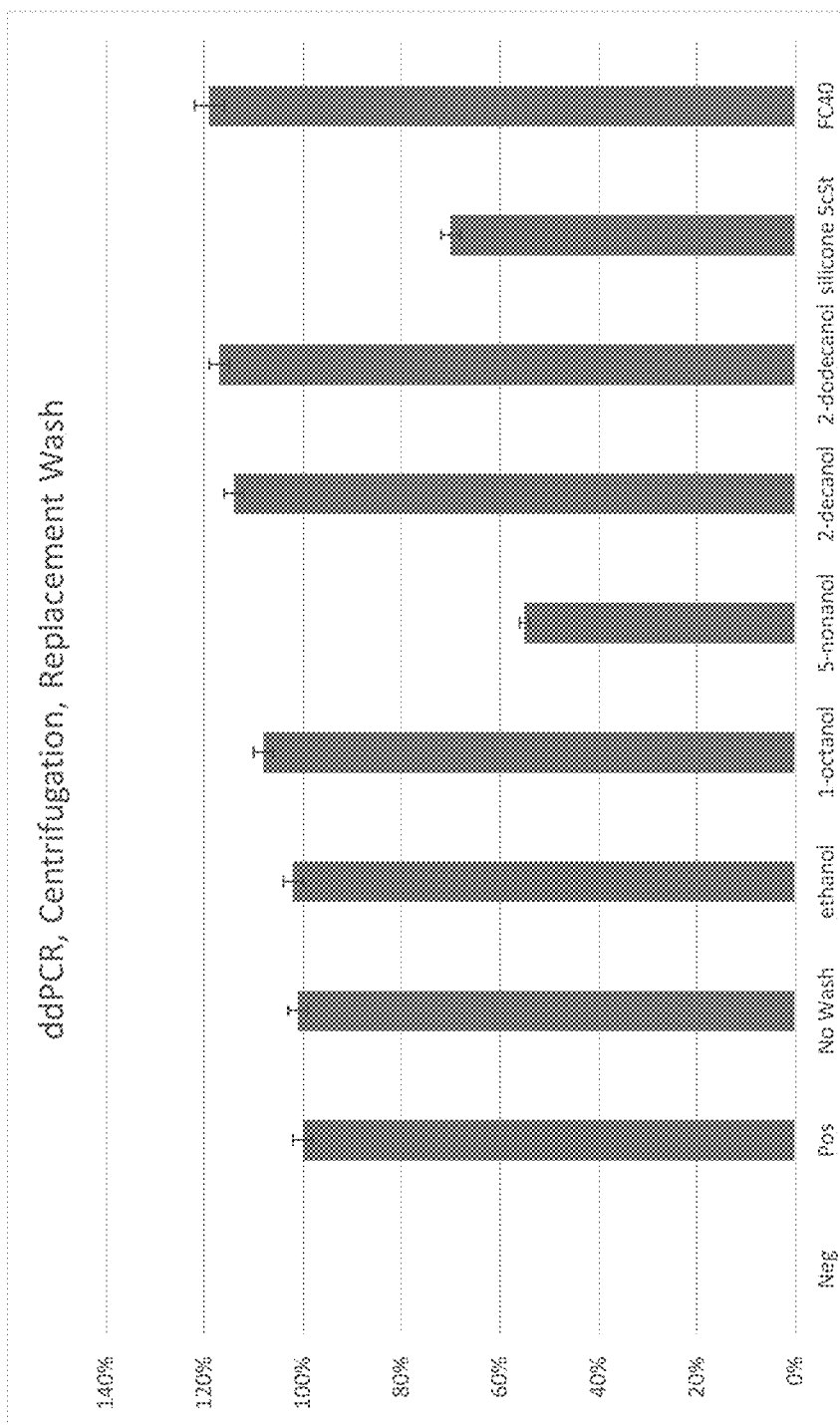
FIG. 7 shows a chart illustrating the results of digital PCR (ddPCR) reactions performed on lambda phage DNA spiked in PBS, extracted with centrifugation using ZR Viral DNA/RNA kit (Pos), or with a modified protocol with a wash step with ethanol, 1-octanol, 5-nonanol, 2-decanol, 2-dodecanol, 5 cSt silicone oil, or FC-40, or no wash step as indicated. In the chart of FIG. 7, the results of the digital PCR amplification is expressed in normalized concentration. In the chart of FIG. 7, error bars represent the standard deviation for n=3.

The results illustrated in FIGS. 6 and 7 show the impact on LAMP reaction and ddPCR reaction of uses of a replacement wash in a procedure comprising centrifugation (which has a low carryover).

In particular, the LAMP results shown in FIG. 6 suggest that the viral wash buffer step is critical because without it, the LAMP assay fails. The LAMP assay can be recovered by replacing the viral wash buffer step with 100% ethanol, 1-octanol, 5-nonanol, 2-decanol, or 2-dodecanol. While silicone oil and FC-40 oil may be used as an additional wash step, they do not work to replace the viral wash buffer.

The ddPCR results illustrated in FIG. 7 suggest that the extraction efficiency is equivalent or better for all conditions with the exception of 5-nonanol and 5 cSt silicone oil. Note that the "No Wash", 5 cSt silicone oil, and FC-40 oil condition do contain nucleic acids (diluted 100-fold and analyzed with ddPCR) implying that nucleic acids are present, but contaminants are also present which inhibit the LAMP reaction (diluted 2-fold).

Example 7: Pressurization

A ZR Viral DNA/RNA kit was modified for use with a 5 mL syringe. A 500 mg/mL solution of purified lambda phage DNA (New England Biolabs, NEB, having 240 County Road, Ipswich, Mass. 01938) was spiked into molecular biology grade phosphate buffered saline (PBS from Corning, having corporate headquarter at one riverfront plaza, Corning, N.Y. 14831) to a final concentration of 5 mg/mL. PBS (no DNA for negative control) was mixed 1:1 with a 2× solution of DNA/RNA Shield™ (Zymo Research).

The resulting mixture was combined with 2 volumes of Viral DNA/RNA lysis buffer (Zymo Research, SKU D7020-1-100) and 500 uL was inserted into a 5 mL syringe wrapped with teflon tape and attached to a Zymo-Spin™ IIC-XL Column (Zymo Research). The syringe was depressed from the 5 mL marking to the 2.5 mL marking and held until 10 s after all of the fluid had evacuated the syringe. The column was disconnected from the syringe and the syringe discarded.

This syringe pumping step was repeated for 500 uL viral wash buffer (Zymo Research), except for one condition in which the viral wash buffer was replaced with 2-dodecanol. For some test conditions, an additional syringe pumping step was added with 300 uL of either 1-octanol, 2-decanol, 2-dodecanol, 5 cSt silicone oil, or FC-40. The aqueous phase was carefully pipetted, and the template diluted 2-fold for each LAMP reaction.

Figure 8:
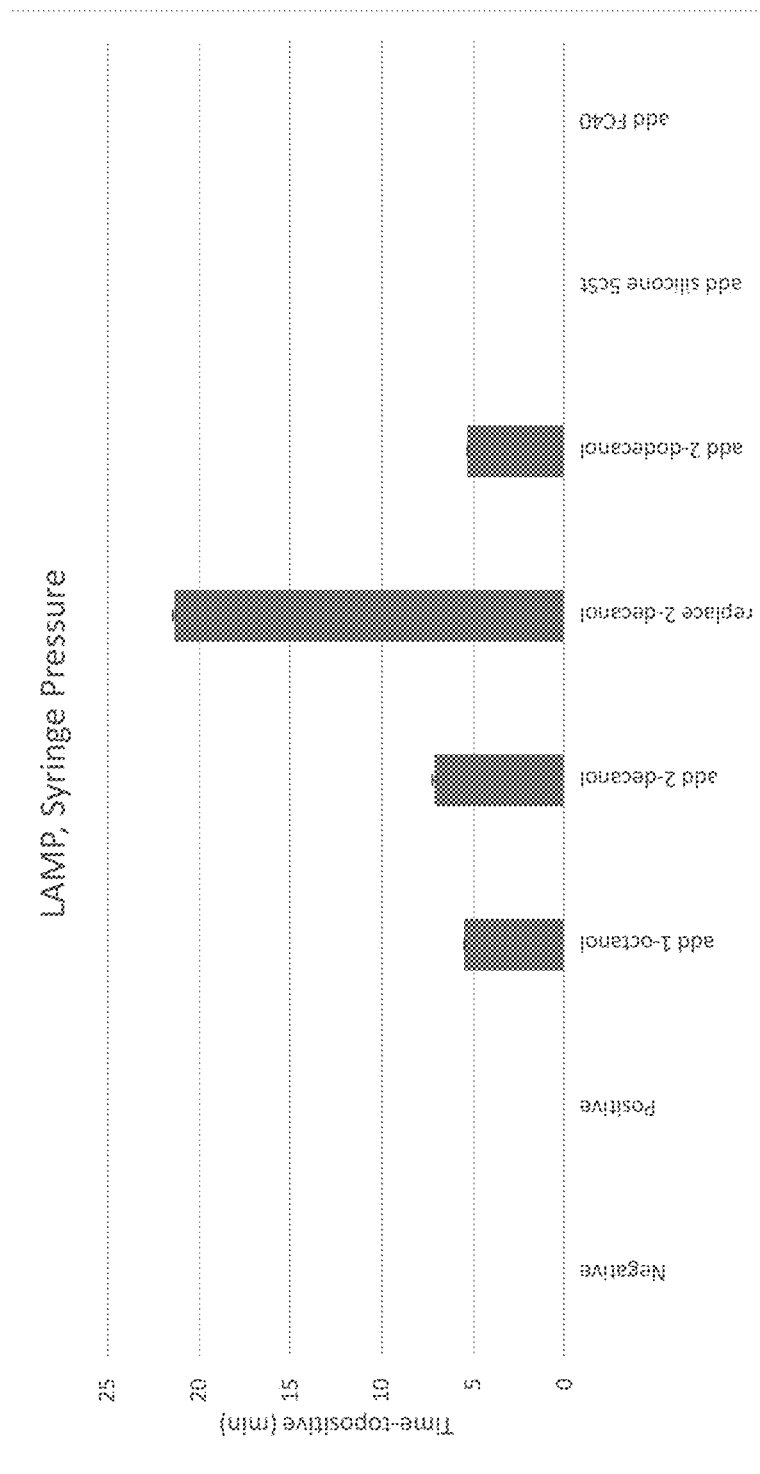
FIG. 8 shows a chart illustrating the results of LAMP reactions performed on lambda phage DNA spiked in PBS, extracted with a ZR Viral DNA/RNA kit modified for syringe pressurization (Pos), comprising a wash step with viral wash buffer followed (add) or replaced (replace) by a wash with 1-octanol, 5-nonanol, 2-decanol, as indicated. In the chart of FIG. 8, the LAMP amplification is expressed in time-to-positive values in minutes wherein time-to-positive of 0 min indicates that there was no amplification for at least 30 min. In the chart of FIG. 8, error bars represent the standard deviation for n=3.

The results illustrated in FIG. 8 show the time to positive value of a LAMP reaction performed on nucleic acid following extraction with pressurization (a procedure that has significant carryover), and downstream analysis with LAMP Protocol.

In particular the results of FIG. 8 show that a positive control where the final step is viral wash buffer does not work. Long-chain alcohols are effective as an additional wash following viral wash buffer to recover LAMP ttp. Replacement of viral wash buffer with 2-decanol recovers LAMP but ttp is later. Silicone 5 cSt and FC40 as an additional wash did not recover LAMP.

The data illustrated in FIG. 8 also show that when using syringe pressure, the positive condition does not amplify with LAMP. This is because there is significant carry-over of the viral wash buffer which completely inhibits the LAMP reaction. However, using 1-octanol, 2-decanol, or 2-dodecanol as an additional wash after the viral wash buffer followed by a 2-phase extraction does recover the LAMP amplification. It is noted that replacing the viral wash buffer with 2-decanol and performing a 2-phase extraction also recovers the LAMP amplification, although the time-to-positive is late. The addition of 5 cSt silicone oil or FC-40 oil as an additional wash after the viral wash buffer does not recover LAMP amplification.

In summary, described herein are Methods and systems and related composition for separating through a solid matrix a mixture comprising a nucleic acid together with a target compounds having a water solubility equal to or greater than 0.001 g per 100 mL, which can be used for managing fluid flow, biochemical reactions and purification of nucleic acids or other target analytes.

In particular, in several embodiments, the methods include solid-phase extraction of analytes such as nucleic acids having a step of washing of a solid matrix such as silica column with a removing agent and related detection reagents, compositions, methods and systems.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified methods and systems based on the target compound removing agents, nucleic acid removing agents, solid matrices, and devices according to various embodiments and scope of the claims.

All patents and publications mentioned in the specification are indicative of the levels of skill of those skilled in the art to which the disclosure pertains.

The entire disclosure of each document cited (including webpages patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure.

Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

The invention claimed is:

1. A system to selectively remove a target compound having a water solubility equal to or greater than 0.001 g per 100 mL from a solid matrix further retaining a nucleic acid, the system comprising:
   a target compound removing agent selected so that the target compound removing agent has a solubility in water equal to or less than 10 g per 100 mL, and that water has a solubility in the target compound removing agent of less than 30 g per 100 mL; and
   the solid matrix configured to retain a nucleic acid.

2. The system of claim 1, further comprising a nucleic acid removing agent.

3. The system of claim 2, wherein the nucleic acid removing agent is selected from nuclease-free water, distilled water, Tris EDTA buffer, DNA Elution Buffer, DNase/RNase-free water and Buffer EB.

4. The system of claim 1, further comprising a reagent to perform a target biochemical reaction.

5. The system of claim 4, wherein the target biochemical reaction is selected from the group comprising PCR, LAMP, strand displacement amplification, helicase-dependent amplification, nicking enzyme amplification reaction, Sequencing, next-generation sequencing, reverse transcription, quality analysis, ligation of sequencing barcodes, cloning, gel electrophoresis, cell-free extract transcription translation, plasmid generation, CRISPR-Cas9, and in-vitro transcription.

6. The system of claim 1, wherein the target compound removing agent has a water solubility equal to or less than 1 g per 100 mL, equal to or less than 0.1 g per 100 mL, equal to or less than 0.01 g per 100 mL, equal to or less than 0.001 g per 100 mL, or equal to or less than 0.0001 g per 100 mL.

7. The system of claim 1, wherein the target compound removing agent comprises a compound of Formula (I):

$$R_1\text{—}Z\text{—}R_2 \qquad \text{Formula (I)}$$

wherein
   Z is selected from the group consisting of —(NR$_{10}$)—, —O—, —S—, —(C=O), —CO$_2$—, —(CONR$_{11}$)— and —(OSiR$_{12}$R$_{13}$O)—;
wherein
   R1 is a linear, branched, substituted or unsubstituted alkyl, alkenyl, alkynyl group containing m number of carbons, wherein m is at least 1;
   R2 is H or a linear, branched, substituted or unsubstituted alkyl, alkenyl, or alkynyl group containing n number of carbons, wherein n is at least 1;
wherein
   R10, R11, R12 and R13 are independently H, linear, or branched alkyl, alkenyl, or alkynyl group containing p number of carbons, wherein p is at least 1 and equal to or less than 4; and
wherein a sum of m, n and p is at least 5.

8. The system of claim 7, wherein
   Z is —O—, —CO$_2$—, or —(CONR$_{11}$)—;
   R1 is selected from the group consisting of a linear, branched, substituted or unsubstituted lower alkyl group, lower alkenyl group, lower alkynyl group, intermediate alkyl group, intermediate alkenyl group, intermediate alkynyl group, higher alkyl group, higher alkenyl group, and higher alkynyl group; and
   R2 is H.

9. The system of claim 8, wherein Z is —O—; and R1 is 1-octyl, 2-ethylhexyl, 1-octyl, 2-octyl, 3-octyl, 4-octyl, 1-nonyl, 2-nonyl, 3-nonyl, 4-nonyl, 5-nonyl, 1-decyl, 2-decyl, 3-decyl, 4-decyl, 5-decyl, 1-undecyl, 2-undecyl, 3-undecyl, 4-undecyl, 5-undecyl, 6-undecyl, 1-dodecyl, 2-dodecyl, 3-dodecyl, 4-dodecyl, 5-dodecyl, or 6-dodecyl group.

10. The system of claim 8, wherein Z is —CO$_2$—; and R1 is 1-octyl, 4-octyl or 2-ethylhexyl group, or a combination thereof.

11. The system of claim 8, wherein the target compound removing agent comprises a compound selected from the group comprising caprylic acid, capric acid, lauric acid, myristic acid, palmitic acid, or stearic acid, cis oleic acid, and trans oleic acid, or a combination thereof.

12. The system of claim 8, wherein the target compound removing agent comprises a compound selected from myristoleic acid, palmitoleic acid, sapienic acid, oleic acids, elaidic acid, vaccenic acid, linoleic acid, linoelaidic acid, α-linolenic acid, and ricinoleic acid, or a combination thereof.

13. The system of claim 8, wherein the target compound removing agent comprises a compound selected from palm oil, coconut oil, canola oil, soybean oil, sunflower oil, rapeseed oil, peanut oil, cotton seed oil, palm kernel oil, and olive oil, or a combination thereof.

14. The system of claim 8, wherein the target compound removing agent is a silicone oil.

15. The system of claim 14, wherein the silicone oil comprises a compound having a linear or cyclic backbone represented by Formula (II):

$$E_1\text{-}[SiR_{14}R_{15}O]_h\text{-}E_2 \qquad \text{Formula (II)}$$

wherein
   R14 and R15 are independently a linear, or branched, substituted or unsubstituted, alkyl, alkenyl, alkynyl, aryl, or alkylaryl containing h number of carbons, wherein h is at least 1 and equal to or less than 20;
   E1 is selected from the group comprising null for cyclic backbone, H, OH, a lower alkyl group of C1-C4;
   E2 is selected from the group comprising null for cyclic backbone, H, a lower alkyl, alenyl or alkynyl group of C1-C4; and
   h is at least 1, 10, 30, 50 or 100.

16. The system of claim 15, wherein the silicone oil comprises a compound of Formula (III):

$$CH_3[Si(CH_3)_2O]_qSi(CH_3)_3 \qquad \text{Formula (III)}$$

wherein q is at least 1, 10, 30, 50 or 100.

17. The system of claim 1, wherein the target compound comprises a buffer agent, an antibiotic, a saccharide, an amino acid, a peptide, a protein or a salt, lysis buffer agent, wash buffer agent, wash buffer agent containing 60-80% ethanol, 100% ethanol, phenols, humic acids, urea, proteases, calcium ions, potassium ions, chloride ions, sodium ions, sodium desoxycholate, sodium dodecyl sulfate, sarkosyl, isopropanol, bile salts, collagen, heme, melanin, eumelanin, myoglobin, lactoferrin, hemoglobin, immunoglobin G, indigo dye, tannic acid, antivirals, heparin, hormones, lipids, urate, algae, glycogen, pectin, xylans, fulmic acids, metal ions, bone dust, peat extract, ethylenediaminetetraacetic acid, cell debris, or detergents or any combination thereof.

18. The system of claim 1, wherein the target compound comprises a chaotropic agent selected from the group consisting of n-butanol, ethanol, guanidinium thiocyanate, guanidinium chloride, lithium perchlorate, lithium acetate, magnesium chloride, phenol, 2-propanol, sodium dodecyl sulfate, thiourea, and urea.

19. The system of claim 17, wherein the buffer agent is selected from the group consisting of N-(2-Acetamido)-aminoethanesulfonic acid (ACES), Salt of acetic acid (Acetate), N-(2-Acetamido)-iminodiacetic acid (ADA), 2-Aminoethanesulfonic acid, Taurine (AES), Ammonia, 2-Amino-2-methyl-1-propanol (AMP), 2-Amino-2-methyl-1,3-propanediol, (Ammediol or AMPD), N-(1,1-Dimethyl-2-hydroxyethyl)-3-amino-2-hydroxypropanesulfonic acid (AMPSO), N,N-Bis-(2-hydroxyethyl)-2-aminoethanesulfonic acid (BES), Sodium Bicarbonate, N,N'-Bis(2-hydroxyethyl)-glycine (Bicine), [Bis-(2-hydroxyethyl)-imino]-tris-(hydroxymethylmethane) (BIS-Tris), 1,3-Bis[tris (hydroxymethyl)-methylamino]propane)(BIS-Tris-Propane), Boric acid, Dimethylarsinic acid (Cacodylate), 3-(Cyclohexylamino)-propanesulfonic acid (CAPS), 3-(Cyclohexylamino)-2-hydroxy-1-propanesulfonic acid (CAPSO), Sodium carbonate, Cyclohexylaminoethanesulfonic acid (CHES), Salt of citric acid (Citrate), 3-[N-Bis (hydroxyethyl)amino]-2-hydroxypropanesulfonic acid (DIPSO), Formate Salt of formic acid, Glycine, Glycylglycine, N-(2-Hydroxyethyl)-piperazine-N'-ethanesulfonic acid (HEPES), N-(2-Hydroxyethyl)-piperazine-N'-3-propanesulfonic acid (HEPPS, EPPS), N-(2-Hydroxyethyl)-piperazine-N'-2-hydroxypropanesulfonic acid (HEPPSO), Imidazole, Salt of malic acid (Malate), Maleate Salt of maleic acid, 2-(N-Morpholino)-ethanesulfonic acid (MES), 3-(N-Morpholino)-propanesulfonic acid (MOPS), 3-(N-Morpholino)-2-hydroxypropanesulfonic acid (MOPSO), Salt of phosphoric acid (Phosphate), Piperazine-N,N'-bis(2-ethanesulfonic acid) (PIPES), Piperazine-N,N'-bis(2-hydroxypropanesulfonic acid) (POPSO), Pyridine, Salt of succinic acid (Succinate), 3-{[Tris(hydroxymethyl)-methyl]-amino}-propanesulfonic acid (TAPS), 3-[N-Tris(hydroxymethyl)-methylamino]-2-hydroxypropanesulfonic acid (TAPSO), Triethanolamine (TEA), 2-[Tris(hydroxymethyl)-methylamino]-ethanesulfonic acid (TES), N-[Tris(hydroxymethyl)-methyl]-glycine (Tricine), and Tris(hydroxymethyl)-aminomethane (Tris), or any combination thereof.

20. The system of claim 1, wherein the solid matrix comprises a silica.

21. The system of claim 20, wherein the silica comprises a gel particle, glass particle, glass microfiber, slurry, magnetic beads, paramagnetic beads, superparamagnetic beads, SPRI beads or any combination thereof.

22. The system of claim 21, wherein the glass particle comprises a powder, microbead, silicate glass, flint glass, borosilicate glass, or glass fiber filter.

23. The system of claim 1, wherein the solid matrix comprises anion exchange solid matrix.

24. The system of claim 23, wherein the anion exchange solid matrix comprises a cationic group represented by Formula (IV):

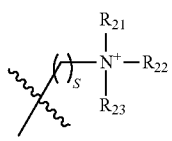

Formula (IV)

wherein
s is 1 to 6, and
R21, R22, and R23 are independent selected from H, linear, branched, substituted or unsubstituted a lower alkyl group (C1-C4).

25. The system of claim 24, wherein the solid matrix comprises a resin, and s is 2 and R21 and R22 are ethyl groups and R23 is a proton.

26. The system of claim 1, wherein the solid matrix has a cylindrical shape of a diameter ranging from 0.1 millimeter to 1 meter and a longitudinal dimension ranging from 0.01 millimeter to 1 meter.

27. The system of claim 1, wherein the solid matrix has a volume of 1 nanoliter to 1 L.

28. The system of claim 1, wherein the solid matrix has a solid matrix volume, the removing agent has a removing agent volume, and the removing agent volume is 1 to 100,000 times or more of the solid matrix volume.

29. The system of claim 1, wherein the target compound removing agent is capable of inhibiting a target enzyme catalyzing a target biochemical reaction of the nucleic acid by a rate of less than 50%.

30. The system of claim 1, wherein the solid matrix is within a column or a tube.

31. The system of claim 30, wherein the solid matrix comprises a magnetic bead.

32. The system of claim 30, wherein the system is used in combination with a device.

33. The system of claim 32, wherein the device is a portable device.

34. The system of claim 30, wherein the target compound removing agent comprises a fluorocarbon.

35. The system of claim 30, wherein the system comprises at least two target compound removing agents.

36. The system of claim 30, further comprising a reagent to perform a target biochemical reaction.

37. The system of claim 30, wherein the target biochemical reaction is a nucleic acid amplification reaction.

38. The system of claim 30, wherein the target biochemical reaction is selected from the group comprising, PCR, LAMP, strand displacement amplification, helicase-dependent amplification, nicking enzyme amplification reaction, Sequencing, next-generation sequencing, reverse transcription, quality analysis, ligation of sequencing barcodes, cloning, gel electrophoresis, cell-free extract transcription translation, plasmid generation, CRISPR-Cas9, and in-vitro transcription.

39. The system of claim 30, wherein the target compound is capable of inhibiting a target enzyme catalyzing a target biochemical reaction of the nucleic acid.

40. The system of claim 30, wherein the target compound removing agent is capable of inhibiting a target enzyme catalyzing a target biochemical reaction of the nucleic acid by a rate of less than 50%.

41. The system of claim 1, wherein the system is in the form of a kit of parts comprising the target compound removing agent and the solid matrix as components of the kit.

* * * * *